US008241610B2

(12) United States Patent
Agger et al.

(10) Patent No.: US 8,241,610 B2

(45) Date of Patent: Aug. 14, 2012

(54) ADJUVANT COMBINATIONS OF LIPOSOMES AND MYCOBACTERIAL LIPIDS FOR IMMUNIZATION COMPOSITIONS AND VACCINES

(75) Inventors: Else Marie Agger, Copenhagen S (DK); Peter Andersen, Brønshøj (DK); Anja Olsen, Søborg (DK); Ida Rosenkrands, Værløse (DK)

(73) Assignee: Statens Serum Institut, Copenhagen S (DK)

(*) Notice: Subject to any disclaimer, the term of this patent is extended or adjusted under 35 U.S.C. 154(b) by 0 days.

(21) Appl. No.: 13/083,385

(22) Filed: Apr. 8, 2011

(65) Prior Publication Data

US 2011/0250224 A1 Oct. 13, 2011

Related U.S. Application Data

(63) Continuation of application No. 10/563,731, filed as application No. PCT/DK2004/000488 on Jul. 7, 2004, now abandoned.

(30) Foreign Application Priority Data

Jul. 9, 2003 (DK) ................................. 2003 01046
Sep. 27, 2003 (DK) ................................. 2003 01403

(51) Int. Cl.
*A61K 9/127* (2006.01)
*A61B 5/055* (2006.01)

(52) U.S. Cl. ....................................... 424/9.34; 424/450

(58) Field of Classification Search ........................ None
See application file for complete search history.

(56) References Cited

U.S. PATENT DOCUMENTS 6,218,166 B1 4/2001 Ravindranath et al.
6,248,329 B1 6/2001 Chandrashekar et al.
2002/0044951 A1 4/2002 Liu et al.
2002/0176867 A1 11/2002 Andersen et al.
2002/0198168 A1 12/2002 Lowrie
2004/0191304 A1 9/2004 Sprott et al.

FOREIGN PATENT DOCUMENTS

WO WO 00/69458 A2 11/2000
WO WO 02/074330 A2 9/2002
WO WO 02/074333 A2 9/2002
WO WO 03/011336 A2 2/2003

OTHER PUBLICATIONS

Andersen et al. (1994) Effective vaccination of mice against *Mycobacterium tuberculosis* infection with a soluble mixture of secreted mycobacterial proteins. Infect. Immun.; 62:2536-2544.
Bowie et al. (1990) Deciphering the message in protein sequences: tolerance to amino acid substitutions. Science; 247:1306-1310.
Dascher et al. (2003) Immunization with a mycobacterial lipid vaccine improves pulmonary pathology in the guinea pig model of tuberculosis. International Immunology; 15(8):915-925.
Greenspan et al. (1999) Defining epitopes: it's not as easy as it seems. Nature Biotechnology; 17:936-937.
Gregoriadis, G. (1995) Engineering liposomes for drug delivery: progress and problems. Trends Biotechnol.; 13:527-537.
Hilgers et al. (1991) DDA as an immunological adjuvant. Res. Immunol.; 143:494-503.
Holten-Andersen et al. (2004) Combination of the Cationic Surfactant Dimethyl Dioctadecyl Ammonium Bromide and Synthetic Mycobacterial Cord Factor as an Efficient Adjuvant for Tuberculosis Subunit Vaccines. Infection and Immunity; 72(3):1608-1617.
Koike et al. (1998) Enhancing activity of mycobacterial cell-derived adjuvants on immunogenicity of recombinant human hepatitis B virus vaccine. Vaccine; 16(20):1982-1989.
Linblad et al. (1994) Adjuvant Modulation of Immune Responses to Tuberculosis Subunit Vaccines. Infection and Immunity; 65(2):623-629.
Moingeon et al. (2001) Towards the rational design of Th1 adjuvants. Vaccine; 19:4363-4372.
Moura et al. (1997) Down-Regulatory Effect *Mycobacterium leprae* Cell Wall Lipids on Phagocytosis, Oxidative Respiratory Bursts and Tumour Cell Killing by Mouse Bone Marrow Derived Macrophages. Scand. J. Immunol.; 46:500-505.
Olsen et al. (2001) Protection of Mice with a 9Tuberculosis Subunit Vaccine Based on a Fusion Protein of Antigen 85B and ESAT-6. Infection and Immunity; 69(5):2773-2778.
Saito et al. (1976) Adjuvant Effect of Cord Factor, a Mycobacterial Lipid. Infection and Immunity; 13(3):776-781.

*Primary Examiner* — Ram R Shukla
*Assistant Examiner* — Nina Archie
(74) *Attorney, Agent, or Firm* — Knobbe Martens Olsen & Bear LLP

(57) ABSTRACT

The present invention provides a vaccine adjuvant consisting of a combination of a surfactant i.e. dimethyldeoctadecylammonium-bromide/chloride (DDA) and a lipid extract from *Mycobacterium bovis* BCG. The total lipid extract contains both apolar lipids, polar lipids, and lipids of intermediate polarity of which the apolar lipids were found to induce the most powerful immune responses. The total lipids may be extracted with chloroform/methanol and re-dissolved in water before the addition of surfactant. This preparation may be used to induce prominent cell-mediated immune responses in a mammal in order to combat pathogens, or as a treatment for cancer.

14 Claims, 11 Drawing Sheets

Figure 6B:
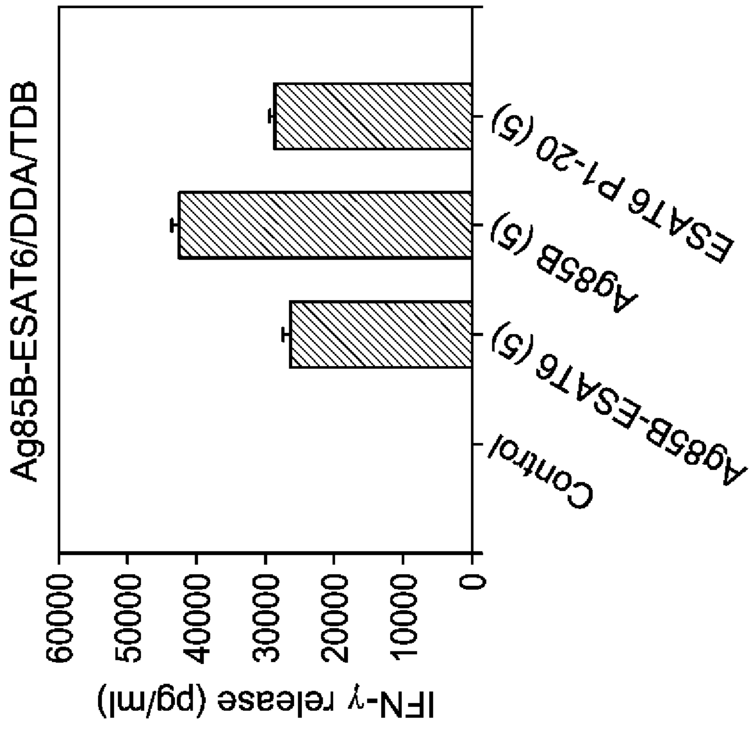
Figure 6A:
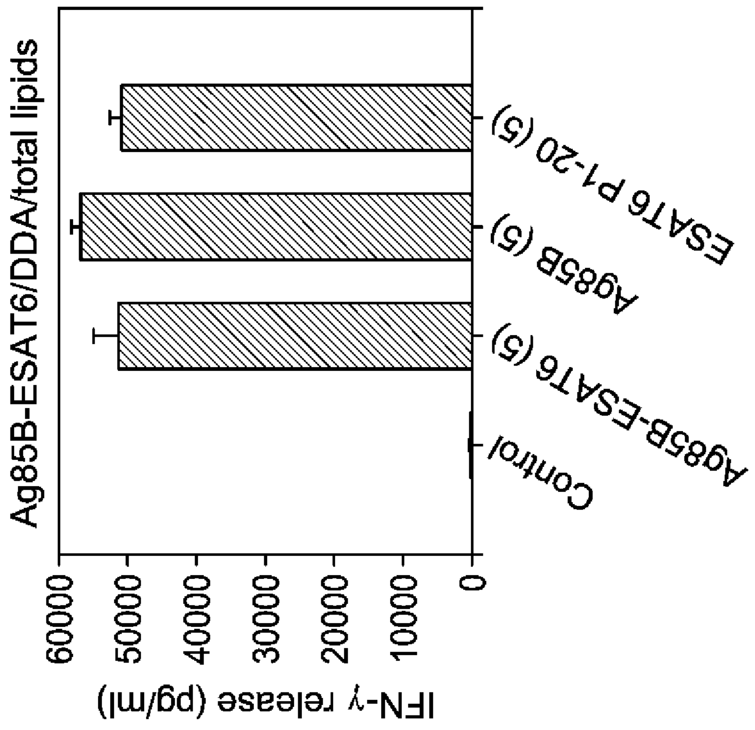

*FIG. 7A* 6 months
*FIG. 7B* 13 months
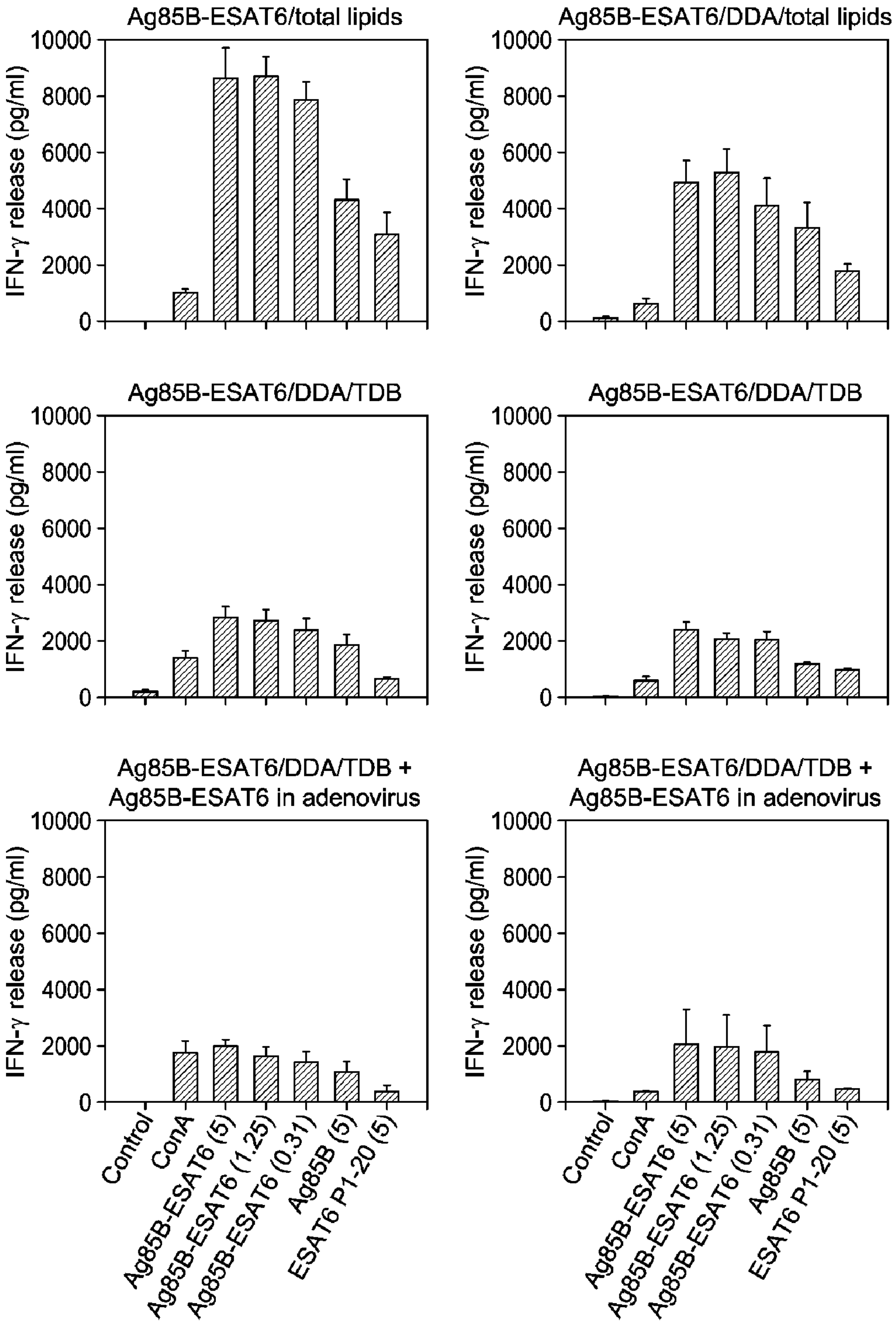

ADJUVANT COMBINATIONS OF LIPOSOMES AND MYCOBACTERIAL LIPIDS FOR IMMUNIZATION COMPOSITIONS AND VACCINES

CROSS-REFERENCE TO RELATED APPLICATIONS

This application is a continuation of and claims priority to U.S. patent application Ser. No. 10/563,731, filed on Jan. 6, 2006, which is the U.S. National Phase filing under 35 U.S.C. §371 of PCT/DK2004/000488, filed Jul. 7, 2004, which designated the United States and was published in English, which claims priority to Danish Patent Application Nos. PA 2003 01046, filed Jul. 9, 2003, and PA 2003 01403, filed Sep. 27, 2003. The contents of these applications are expressly incorporated herein by reference in their entireties.

FIELD OF INVENTION

The present invention discloses an adjuvant comprising a surfactant and the total lipid extract of the BCG mycobacterium as well as the apolar fraction thereof and a vaccine comprising said adjuvant and an antigenic substance.

BACKGROUND OF THE INVENTION

The first vaccines consisted of live, attenuated pathogens. The attenuated forms were either naturally occurring closely related organisms or obtained through serial passages in culture. For example, tuberculosis (TB) in man has for many years been combated by vaccination with an attenuated strain of *Mycobacterium bovis*, the *M. bovis* BCG vaccine developed more than 80 years ago. However, although more than 3 billion doses of BCG have been administered (more than any other vaccine) (Bloom and Fine, 1994), it does not always provide satisfactory resistance to humans TB in every population.

Today, a more up-to-date approach is to use highly purified substances, e.g. purified recombinant proteins. These vaccines are well-defined and side-reactions are minimized. Unfortunately, many highly purified substances are not very immunogenic and do not induce a sufficient immune response to confer protection. To do this, the antigen needs some help from immune response potentiating agents called adjuvants. Depending on the pathogen, protection may require that either a humoral or a cell-mediated response predominate. The development of a specific kind of immune response (humoral or cell-mediated) can be determined by the choice of adjuvant.

Protective immunity against an intracellular pathogen like *M. tuberculosis* requires a cell-mediated immune response, and a suitable adjuvant for a subunit vaccine directed against TB should enhance a Th1 response (Lindblad et al, 1997). It is generally believed that antibodies do not play an important role in immunity to TB whereas cell-mediated release of IFN-gamma (interferon gamma) is the most important cytokine involved in protection (Collins & Kaufmann, 2001).

A large number of adjuvants exist but most of these suffer from numerous problems that preclude their use in humans. The only adjuvants accepted for human use are aluminum-based adjuvants (AlOH-salts) and MF-59, but they both induce Th2-biased responses, which makes them unsuitable for a TB vaccine (Lindblad et al, 1997).

During the past 20-30 years a number of new adjuvant systems have been identified. One example is QS-21, which is a highly purified compound isolated from the bark of the South American tree *Quillaja saponaria*. QS-21 is a potent adjuvant with low toxicity (Kensil et al, 1991). Lack of ease of production and a high price may be an important issue for QS-21 and other novel, promising adjuvant compounds. Despite the fact that many adjuvant systems have been developed, the need for new adjuvant systems is still recognized (Moingeon et al, 2001) and is evident in the paucity of choices available for clinical use.

Various compounds from mycobacteria have been reported to be immunepotentiating. When lipids extracted from *M. bovis* BCG were used as adjuvant, a skin test response to ovalbumin was obtained in guinea pigs (Hiu, 1975). Liposomes formed at elevated temperatures from total polar lipids of *M. bovis* BCG are able to generate a humoral response to ovalbumin, and a vaccine prepared from these polar lipids gave protection in mice upon challenge with tumor cells (WO 03/011336). The effect of total lipids from *M. tuberculosis* H37Rv as antigen in an experimental TB vaccine for guinea pigs was investigated by Dascher et al (2003). In this study, liposomes based on cholesterol and 1,2-distearoyl-sn-glycero-3-phosphocholine (DSPC) were mixed with a *M. tuberculosis* H37Rv total lipid extract. After removing the solvent, the lipids were reconstituted with DDA as an adjuvant in PBS buffer. Guinea pigs immunised with this vaccine did not show significant reduction in bacteria, suggesting that this formulation of liposomes mixed with DDA lack a strong antigen or that the formulation of mycobacterial lipids with Cholesterol: DSPC prevent the adjuvenating effect of DDA.

Various purified components from mycobacteria have also been investigated for their adjuvant activity. Purified protein derivative (PPD) did not induce delayed type hypersensitivity reaction on its own, but when Wax D (a mycobacterial cell wall peptidoglycan fragment-arabinogalactan-mycolic acid complex) was added as adjuvant, a strong reaction was observed (Yamazaki, 1969). The immunomodulator SSM or Z-100, a lipid arabinomannan extracted from *M. tuberculosis*, has antitumor activity (Suzuki et al, 1986). Another mycobacterial cell-derived compound is trehalose 6,6'-dimycolate (cord factor; a mycolic acid containing glycolipid) (Saito et al, 1976). Also, trehalose 6,6'-dimycolate (or synthetic analogues) has immunostimulatory effects and has been included in various adjuvant formulations (McBride et al, 1998; Koike et al, 1998). Taken together, several immunostimulating lipid compounds have been isolated from mycobacteria, but the laborious and thereby expensive purification schemes required makes them unlikely to be included in a future TB vaccine.

Adjuvants exist in many different forms, some of which are surfactant-like and form liposomes, which are vesicles made up of lipid bilayers. The liposomes act as carriers of the antigen (either within the vesicles or attached onto the surface) and may form a depot at the site of inoculation allowing slow, continuous release of antigen. For some time after injection and phagocytosis, liposomal presentation ensures that a specific amount of antigen is made available to single antigen-presenting cells (Glück, 1995). The adjuvant activity of liposomes applies to, a large variety of pathogens (Gregoriadis et al, 2000), and more recently prominent anti-tumor responses characterized by cytotoxic CD8 T cell responses were elicited with therapeutic vaccines adjuvanted with cationic lipids (Siders et al, 2002).

Dimethyldioctadecylammonium-bromide, -chloride, -phosphate, -acetate or other organic or inorganic salts (DDA) is a lipophilic quaternary ammonium compound, which forms cationic liposomes in aqueous solutions at temperatures above 40° C. It promotes cell mediated immunity (Hilgers & Snippe, 1992). Combinations of DDA and other immunomodulating agents have been described. Administration of Arquad 2HT, which comprises DDA, in humans were promising and did not induce apparent side effects (Stanfield, 1973). An experimental vaccine based on culture filtrate proteins from *M. tuberculosis* and DDA generated a protective immune response against TB in mice (Andersen, 1994). Vaccination of mice with a fusion protein of *M. tuberculosis* proteins ESAT-6 and Ag85B, and DDA/MPL as adjuvant, provides protection similar to that obtained by BCG vaccination (Olsen et al, 2001). These studies demonstrate that, in contrast to e.g. alum, DDA-based adjuvants are able to induce a protective immune response against TB in mice. Moreover, DDA has been used as an adjuvant for a DNA vaccine against pseudorabies virus leading to enhanced T-cell responses and anti-viral immunity (van Rooij et al, 2002). DDA is therefore a promising choice for development of an adjuvant system for a vaccine against TB and other intracellular pathogens.

As indicated above, new adjuvant systems are clearly required. The ideal adjuvant system, which is the subject matter of the present invention, is cheap and easy to produce, it generates a long-lasting protective, immune response of the right type (Th1 or Th2 depending on the pathogen), it does not elicit unacceptable local reactions, it offers long-term stable presentation of the antigen (depot effect) and it helps to target immune cells.

SUMMARY OF THE INVENTION

In the present invention it is demonstrated that a surprisingly high protective immune response is obtained when lipids extracted from *M. bovis* BCG are used as adjuvant together with the cationic surfactant. A greatly increased protective immune response is obtained when DDA is added to a total lipid extract of *M. bovis* BCG, compared to that obtained using either of the components alone, showing a synergistic adjuvant effect of DDA and the total lipid extract. The combination of DDA and total lipids extracted from *M. bovis* BCG gives an even higher protective immune response than DDA/TDB, another combination previously shown to have unexpectedly high efficacy (Holten-Andersen et al, 2004). Furthermore, the total lipid extract does not require extensive purification rendering it cheap to produce and therefore appropriate for inclusion in future vaccines suitable for use throughout the world. It is further shown that the apolar fraction of the total lipid extract has a stronger adjuvant effect than the polar fraction when they are mixed with DDA.

Lipid extracts comprising total, apolar and polar lipids of *M. bovis* BCG were obtained by extraction with organic solvents. The lipid fractions were characterized by thin layer chromatography. The lipid extract was brought into aqueous suspension and mixed with liposomes of a surfactant, e.g. DDA, and an antigen. It was demonstrated that the majority of antigen was bound to the adjuvant fraction. Mice immunized with a fusion protein of ESAT-6 and Ag85B from *M. tuberculosis* together with DDA/BCG lipids, generated a strong immune response, and when used as a vaccine, a protective immune response against *M. tuberculosis* was obtained.

DETAILED DISCLOSURE OF THE INVENTION

The present invention discloses an adjuvant comprising a surfactant and a lipid extract of a mycobacterium, e.g. the BCG, *M. microti, M. tuberculosis* and *M. vaccae.*

The invention further discloses the use of the total lipid extract of the mycobacterium and a surfactant as an adjuvant for a vaccine formulation.

The present invention also discloses an adjuvant comprising a surfactant and a lipid extract comprising the apolar fraction or parts of the apolar fraction of the total lipid extract of a mycobacterium, e.g. BCG, *Mycobacterium microti, M. tuberculosis* and *M. vaccae*. The parts of the apolar fraction of the lipid extract can be phthiocerol dimycocerosates, trehalose mycolipenates, glycosylated phenol phthiocerols (including phenolic glycolipids, PGL's), trehalose mycolates, sulfolipids, triacylglycerols or menaquinones.

The surfactant of the invention is preferably a cationic surfactant.

The surfactant is preferably dimethyldioctadecylammonium-bromide, -chloride, -phosphate or -acetate (DDA), dimethyldioctadecenylammonium -bromide, -chloride, -phosphate or -acetate (DODA), N-[1-(2,3-Dioleoyloxy)propyl]-N,N,N-trimethylammonium-chloride (DOTAP), Cholesteryl 3b-N-(dimethylaminoethyl)carbamate hydrochloride (DC Chol), 1,2-Dioleoyl-sn-glycero-3-phosphoethanolamine and L-Phosphatidylcholine (DOPE/PC) or DOPE/PC/PG (PG is L-alpha-Phosphatidyl-DL-glycerol sodium salt).

The surfactant is most preferably dimethyldioctadecylammonium-bromide or -chloride (DDA), The present invention also discloses a vaccine against infectious diseases, e.g. intracellular pathogens like TB comprising the above mentioned adjuvant and an antigenic substance derived from the infectious agent to be vaccinated against, e.g. a peptide, protein or lysate.

A preferred embodiment of the invention is a vaccine comprising the adjuvant of the invention together with a peptide from a virulent mycobacterium, e.g. *Mycobacterium tuberculosis, M. bovis* or *M. africanum*, where the most preferred antigen is the ESAT6-Ag85B hybrid or a fragment hereof.

Another embodiment of the invention is a vaccine comprising the adjuvant of the invention for treating cancer.

Still another embodiment of the invention is a delivery system comprising the adjuvant.

A general procedure for extraction of total lipids is extraction with chloroform/methanol (2:1) according to Folch (Folch, 1957). In the present invention, this method was used for total lipid extraction. Polar and apolar lipids were obtained by the methods previously described for analysis of mycobacterial lipids (Dobson et al, 1985). A total lipid, an apolar lipid and a polar lipid extract of *M. bovis* BCG was prepared and characterized by thin layer chromatography. The lipid extracts are suspended in water and a homogenous preparation made by probe sonication. Thereafter, antigen of choice is added and finally combined with a surfactant, e.g. DDA.

The adjuvant activity of the lipid fractions was tested together with DDA as a TB vaccine in mice. The apolar fraction showed a stronger adjuvant effect than the polar fraction when combined with the surfactant DDA.

Other liposome forming compounds comprise e.g dimethyldioctadecenylammonium-bromide, -chloride, -phosphate or -acetate (DODA), N-[1-(2,3-Dioleoyloxy)propyl]-N,N,N-trimethylammonium chloride (DOTAP), Cholesteryl 3b-N-(dimethylaminoethyl)carbamate hydrochloride (DC-Chol), 1,2-Dioleoyl-sn-glycero-3-phosphoethanolamine and L-Phosphatidylcholine (DOPE/PC) or DOPE/PC/PG (PG is L-alpha-Phosphatidyl-DL-glycerol).

The adjuvant is added to the antigenic substance and used as a vaccine. In principle the antigenic substance may be any pure chemical species such as a protein or a fragment thereof or artificial mixtures prepared of such species. But it can also be any naturally occurring mixture of chemical species such as e.g. a cell homogenate or fractions thereof, a culture filtrate from microorganisms or cell tissues from multicellular organisms, e.g. higher animals.

Specifically the antigenic substance may be derived from a culture of metabolising *Mycobacterium tuberculosis, Mycobacterium bovis* and other environmental mycobacteria such as e.g. *Mycobacterium avium*. A particular interesting substance from the filtrate of such Mycobacteria is the ESAT-6 protein (Early Secretory Antigenic Target), which is a dominant target for cell mediated immunity in the early phase of TB in TB patients and in different animal models. It contains 95 amino acid residues and has a deduced molecular mass of approximately 10 kDa. Its immunogenicity per se is low, but in combination with the adjuvant combinations of the present invention it has turned out to be a potent candidate for provoking high and persisting immunity against TB as is demonstrated in the following detailed part of this specification.

ESAT-6 as well as many other antigens applicable in combination with the adjuvant combinations of the present invention, today can be produced artificially, e.g. synthetically or by genetic recombinant techniques. A preferred antigen against TB is the ESAT6-Ag85B fusion protein.

The adjuvant of the present invention, and hence the vaccine comprising this adjuvant, possesses all the characteristics wanted from an ideal adjuvant:

- it is cheap and easy to produce
- it generates a long lasting protective, cell-mediated immune response
- it does not elicit unacceptable local reactions, e.g. granulomas
- it helps to target immune cells Furthermore, it was surprisingly discovered that only the adjuvant comprising DDA and the total lipid extract from mycobacteria were capable of inducing a dominant Th1 immune response in a Th2 prone mouse strain in which a Th1 response is not easily generated.

Also the memory immunity was extremely prolonged when using a vaccine comprising DDA and the total lipid extract together with a mycobacterial antigen. The immunity was effective for more than 6 months in mice (in some mice for 14 months).

DEFINITIONS

An adjuvant is defined as a substance that non-specifically enhances the immune response to an antigen. Depending on the nature of the adjuvant it can promote either a cell-mediated immune response, a humoral immune response or a mixture of the two. Since the enhancement of the immune response is non-specific, it is well understood in the field that the same adjuvant can be used with different antigens to promote responses against different targets e.g. with an antigen from *M. tuberculosis* to promote immunity against *M. tuberculosis* or with an antigen derived from a tumor, to promote immunity against tumors of that specific kind.

A total mycobacterial lipid extract is a mixture of lipids obtained from a mycobacteria, e.g. BCG, *M. microti, M. tuberculosis* and *M. vaccae*, by a chemical or physical process. In the present work, the method used for extraction is the action of organic solvents (as described below), but other possibilities, known to those skilled in the art are possible.

The apolar lipid fraction is defined as non-polar lipids. The apolar lipid fraction is obtained by treating mycobacteria with a biphasic mixture of methanol/saline and petroleum ether. The petroleum ether extract is composed of apolar (non-polar) lipids. Hereafter, the polar lipid fraction is obtained by addition of chloroform to mycobacteria and the residual aqueous phase. The chloroform extract contains the remaining polar lipids. The major components in the apolar lipid fraction are phtiocerol dimycocerosates, triacylglycerols, trehalose mycolipenates and menaquinones. The major components of the polar lipid fraction are phospholipids such as phosphatidylethanolamine, phosphatidylglycerol, and phosphatidylinositol (including mannosylated species). Lipids of intermediate polarity are sulpholipids, trehalose mycolates, glycosylated phenolphthiocerols (including phenolic glycolipids, PGL's) and acylated trehaloses, and they are usually found in the apolar lipid fraction (Dobson et al, 1985).

A surfactant (surface-active agent) is a compound such as detergent that can reduce the surface tension of a liquid and may allow it to penetrate e.g. lipid bilayer membranes. Surfactants are amphiphilic substances comprising in its molecule, at the same time one or more hydrophilic groups and one or more hydrophobic groups. Cationic surfactants are often quaternary ammonium salts and the active part of the molecule is a positive ion (cation).

Liposomes (or lipid vesicles) are aqueous compartments enclosed by a lipid bilayer. The lipid components are usually phospholipids or other amphiphiles such as surfactants, often supplemented with cholesterol and other charged lipids. Liposomes are able to entrap water- and lipid-soluble compounds thus allowing the liposome to act as a carrier. Liposomes have been used as delivery systems in pharmacology and medicine such as immunoadjuvants, treatment of infectious diseases and inflammations, cancer therapy, and gene therapy (Gregoriadis, 1995). Factors which may have an influence on the adjuvant effect of the liposomes are liposomal size, lipid composition, and surface charge. Furthermore, antigen location (e.g., whether it is adsorbed or covalently coupled to the liposome surface or encapsulated in liposomal aqueous compartments) may also be important.

An antigenic component or substance is a molecule, which reacts with preformed antibody and/or the specific receptors on T and B cells. In the context of vaccination, a molecule that can stimulate the development of specific T or B cells, leading to the formation of a memory population of immune cells that will promote a faster "memory" response if the antigen is encountered a second time by immune cells. Since memory populations are rarely clonal, in practice this means that an antigen is any molecule or collection of molecules, which can stimulate an increase in immune responses when it is re-encountered by immune cells from an individual who has previously been exposed to it.

The antigenic component or substance can be a polypeptide or a part of the polypeptide, which elicits an immune response in an animal or a human being, and/or in a biological sample determined by any of the biological assays described herein. The immunogenic portion of a polypeptide may be a T-cell epitope or a B-cell epitope. In order to identify relevant T-cell epitopes which are recognised during an immune response, it is possible to use a "brute force" method: Since T-cell epitopes are linear, deletion mutants of the polypeptide will, if constructed systematically, reveal what regions of the polypeptide are essential in immune recognition, e.g. by subjecting these deletion mutants e.g. to the IFN-gamma assay described herein. Another method utilises overlapping oligopeptides (preferably synthetic having a length of e.g. 20 amino acid residues) derived from the polypeptide. These peptides can be tested in biological assays (e.g. the IFN-gamma assay as described herein) and some of these will give a positive response (and thereby be immunogenic) as evidence for the presence of a T cell epitope in the peptide. B-cell epitopes can be determined by analysing the B cell recognition to overlapping peptides covering the polypeptide of interest as e.g. described in Harboe et al, 1998.

Although the minimum length of a T-cell epitope has been shown to be at least 6 amino acids, it is normal that such epitopes are constituted of longer stretches of amino acids. Hence, it is preferred that the polypeptide fragment of the invention has a length of at least 7 amino acid residues, such as at least 8, at least 9, at least 10, at least 12, at least 14, at least 16, at least 18, at least 20, at least 22, at least 24, and at least 30 amino acid residues. Hence, in important embodiments of the inventive method, it is preferred that the polypeptide fragment has a length of at most 50 amino acid residues, such as at most 40, 35, 30, 25, and 20 amino acid residues. It is expected that the peptides having a length of between 10 and 20 amino acid residues will prove to be most efficient as diagnostic tools, and therefore especially preferred lengths of the polypeptide fragment used in the inventive method are 18, such as 15, 14, 13, 12 and even 11 amino acids.

A vaccine is defined as a suspension of dead, attenuated, or otherwise modified microorganisms (bacteria, viruses, or rickettsiae) or parts thereof for inoculation to produce immunity to a disease. The vaccine can be administered either prophylactic to prevent disease or as a therapeutic vaccine to combat already existing diseases such as cancer or latent infectious diseases but also in connection with allergy and autoimmune diseases. The vaccine can be emulsified in a suitable adjuvant for potentiating the immune response.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 μg to 1000 μg, such as in the range from about 1 μg to 300 μg, and especially in the range from about 10 μg to 50 μg. Suitable regimens for initial administration and booster shots are also variable but are typified by an initial administration followed by subsequent inoculations or other administrations.

The manner of application may be varied widely. Any of the conventional methods for administration of a vaccine are applicable. These are believed to include oral or mucosal application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

The vaccines are conventionally administered parenterally, by injection, for example, either subcutaneously or intramuscularly. Additional formulations which are suitable for other modes of administration include suppositories and, in some cases, oral or mucosal formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95% of active ingredient, preferably 25-70%.

The vaccine of choice can e.g. be:

Protein Vaccine

A vaccine composition comprising a polypeptide (or at least one immunogenic portion thereof) or fusion polypeptide.

DNA Vaccine

The nucleic acid fragments of the invention may be used for generating in vivo expression of antigens, i.e. the nucleic acid fragments may be used in so-called DNA vaccines.

Live Recombinant Vaccines

Expression of the relevant antigen in a vaccine in a non-pathogenic microorganism or virus. Well-known examples of such microorganisms are *Mycobacterium bovis* BCG, *Salmonella* and *Pseudomonas* and examples of viruses are Vaccinia Virus and Adenovirus.

Dendritic Cells as Antigen Delivery Vehicles

Loading of antigen to antigen-presenting cells, such as dendritic cells, have shown to be an effective method for generating active T-cells with a role in antitumor immunity.

For all of these vaccine constructs, the addition of a suitable adjuvant has resulted in enhanced vaccine efficacies (Brandt, 2000; van Rooij, 2001; Wang, 2002; Eriksson, 2003).

EXAMPLES

Materials and Methods

Extraction of Total Lipids from *M. bovis* BCG

BCG total lipids were extracted from 12.7 g (wet weight) *M. bovis* BCG Danish 1331 heat inactivated for 1½ hour at 60° C. The bacteria were extracted with 30 millilitres Chloroform/Methanol (2:1) for 15 min. at 55° C. followed by centrifugation (2,000 g, 10 min.). The aqueous phase was removed and the organic phase was collected. The extraction of bacteria was repeated, and the organic phase was collected. The organic phases from both extractions were washed with 5 millilitres of Milli Q water followed by centrifugation (2,000 g, 10 min). The washing of the organic phase was repeated once. After evaporation of the solvent, the amount of dry lipid material was weighed (approx. 300 milligrams), re-dissolved in Chloroform:Methanol (2:1), and aliquoted into vials, and after evaporation of the solvent the dry material in each vial was weighed and stored at −20° C.

Extraction of Polar and Apolar Lipids from *M. bovis* BCG 12.5 g (wet weight) *M. bovis* BCG Danish 1331 was heat inactivated for 1½ hour at 60° C., and 80 millilitres of Methanol:0.3% NaCl (10:1)+40 millilitres Petroleum ether were added. After vigorous agitation for 15 min phase separation was obtained, and the upper organic phase was removed. The lower aqueous phase was extracted with 30 millilitres Petroleum ether, and after phase separation the upper phase was collected and pooled with the previous upper phase. The pooled upper organic phases contained the apolar lipids.

The lower phase was added 56 millilitres Chloroform: Methanol:0.3% NaCl (9:10:3), and extracted by vigorous agitation for one hour followed by centrifugation (750 g, 15 min), and the supernatant was collected. The pellet was resuspended in 5.6 millilitres Chloroform:Methanol:0.3% NaCl (5:10:4), agitated for 30 min. followed by centrifugation (750 g, 15 min), and the supernatant was pooled with the previous supernatant. 19.5 millilitres Chloroform:0.3% NaCl (50:50) was added to the pooled supernatants, followed by mixing for 5 min. and centrifugation (750 g, 10 min.). The lower phase which contained the polar lipids was collected.

After evaporation of the solvent from the extracts containing the apolar and polar lipids, respectively, the amount of dry lipid material was weighed and stored at −20° C.

Thin Layer Chromatography of Lipids from *M. bovis* BCG

BCG total lipid extract was dissolved in Chloroform: Methanol (2:1) and spotted on 2D thin layer chromatography (TLC) plates (0.7 milligrams lipid per plate for non-polar lipids and 1.4 milligrams per plate for polar lipids and lipids of intermediate polarity).

Non-polar lipids were analysed in the following system: $1^{st}$ direction petroleum ether (b.p. 40-60° C.):Ethyl acetate (98:2, 3 developments). $2^{nd}$ direction petroleum ether (b.p. 40-60° C.):Acetone (98:2). Non-polar lipids were detected with 20% molydophoporic acid in ethanol and heated at 120° C.

Polar lipids were analysed in the following system: $1^{st}$ direction chloroform:methanol:water (60:30:6). $2^{nd}$ direction chloroform-acetone-methanol-water (47:25:3:5). Polar lipids were detected with 20% molydophoporic acid in ethanol and heated at 120° C., Ninhydrin reagent was used to detect lipids with free amino groups, and Phospray (Supelco) was used to detect phospholipids.

Glycolipids of intermediate polarity were analysed in the following system: $1^{st}$ direction chloroform:methanol:water (100:14:0.8). $2^{nd}$ direction chloroform:acetone:methanol:water (50:60:2.5:3). Glycolipids were detected by alpha-naphthol reagent and heating at 110° C. for 5 minutes.

Animals

Female BALB/C or C57BL/6 mice, 8 to 12 weeks old, were obtained from Bomholtgaard (Ry, Denmark). Infected mice were kept in cages contained within a BL-3 laminar flow safety enclosure.

Bacteria

*M. tuberculosis* Erdman was grown at 37° C. in modified Sauton medium enriched with 0.5% sodium pyruvate and 0.5% glucose. BCG Danish 1331 was obtained as a freeze-dried vaccine from the SSI, Copenhagen, Denmark and was rehydrated with phosphate-buffered saline (PBS). *M. tuberculosis* H37Rv, *M. bovis* BCG Russia and BCG Pasteur were obtained from the mycobacterial strain collection at Statens Serum Institut.

Adjuvants and Vaccines

*M. bovis* BCG Total Lipids, Polar or Apolar Lipids as Adjuvants:

Total lipids, purified polar, or apolar lipids were prepared by re-dissolving dry lipid material with Milli Q water at 1 or 5 milligrams/millilitre followed by probe sonication (2 pulses of 30 sec).

Twenty four hours before immunization, the antigen was mixed with 0.9% saline and added to total lipids, purified polar, or apolar lipids. In some instances, dimethyldeoctadecylammonium-bromide was added as well, and the final suspension mixed using a vortex mixer. The vaccine was left overnight for incorporation of the antigen.

Dimethyldeoctadecylammonium-bromide (In the following abbreviated to DDA, Eastman Kodak, Inc., Rochester, N.Y.):

DDA was added to sterile water (2.5 milligrams/millilitre) and heated to 80° C. while stirring continuously on a magnetic stirring hotplate for 20 min and allowed to cool before use. Only freshly made DDA was used for immunisation.

Vaccines with DDA as well as total lipids, purified polar, or apolar lipids were prepared as described above. Vaccines with DDA alone were prepared one hour before immunization as previously described (Brandt et al, 2000).

Alternatively, the antigen of choice and total lipids, polar, or apolar lipids can be mixed with 0.9% saline before the generation of DDA liposomes. In this case, the mixture of antigen, total lipids, and DDA is only heated to 40° C. to avoid denaturation of the antigen.

N-[1-(2,3-Dioleoyloxy)propyl]-N,N,N-trimethylammonium chloride (In the following abbreviated to DOTAP, Sigma Aldrich) was dissolved in chloroform, 10 milligrams/milliliter. 1250 micrograms were dried and hydrated with 500 microliters of infection grade water and sonicated in a bath-type sonicator for 30 minutes. Ten micrograms of the antigen in 100 microliters of 50 mM ammoniumbicarbonate buffer and 500 micrograms of total lipids in 500 microliters of infection grade water were added followed by lyophilization. The lipid-antigen mixture was rehydrated by addition of 1000 microliters of saline. For immunization each mouse received 2 micrograms of antigen encapsulated in 250 micrograms of liposome.

Cholesteryl 3b-N-(dimethylaminoethyl)carbamate hydrochloride (In the following abbreviated to DC Chol, Sigma Aldrich) was dissolved in chloroform, 10 mg/ml. 1250 micrograms were dried and hydrated with 500 microliters of infection grade water and sonicated in a bath-type sonicator for 30 minutes. The antigen was encapsulated as described above for DOTAP.

Neutral liposomes were made by mixing L-Phosphatidylcholine (In the following abbreviated to PC, Sigma Aldrich) with 1,2-Dioleoyl-sn-glycero-3-phosphoethanolamine (In the following abbreviated to DOPE, Sigma Aldrich) in the molar ratio of 1:0.5. PC and DOPE were dissolved in chloroform (10 milligrams/milliliter. 1250 micrograms of total lipid were dried and hydrated with 500 microliters of infection grade water and sonicated in a bath-type sonicator for 30 minutes. The antigen was encapsulated as described above for DOTAP.

Cationic liposomes were made by mixing PC, DOPE and Phosphatidylglycerol (In the following abbreviated to PG, Sigma Aldrich) in the molar ratio of 1:0.5:0.25. PC, DOPE and PG were dissolved in chloroform (10 milligrams/milliliter. 1250 micrograms of total lipid were dried and hydrated with 500 microliters of infection grade water and sonicated in a bath-type sonicator for 30 minutes. The antigen was encapsulated as described above for DOTAP.

D-(+)-Trehalose 6,6'dibehenate (in the following abbreviated to TDB, Sigma Biochemicals, US):

TDB was suspended in sterile distilled water containing 2% dimethyl sulfoxide to a concentration of 5 milligrams/millilitre by repeated passage through a fine-tipped pipette followed by 30 seconds of vortexing. The solution was kept at −20° C. until use.

One hour before immunization, antigen was mixed with saline and TDB added. Finally, DDA was added and the final suspension mixed using a vortex mixer.

Alhydrogel 2% (Statens Serum Institut, Copenhagen, Denmark):

Immediately before immunization, the antigen was mixed with saline and added to Alhydrogel.

Montanide ISA720 (Seppic, France):

Immediately before immunization, the antigen is mixed with saline and subsequently mixed with 70% Montanide ISA720 using a micro-emulsifying needle (Fischer Scientific) to prepare a homogenous preparation.

The adenovirus construct expressing Ag85B-ESAT6 was produced by amplifying the fusion protein by PCR from an expression plasmid (pMCT6) as a 1322 bp fragment retaining the His-tag. Primers (forward: 5'-caggatc_ctaGCgaggtttaaatATGg; reverse: 5'-catcacagtatcgtgat_CTagaggcaggg) introduced NheI and Xba I.

Recombinant replication-defective adenovirus was produced in vitro using the Adeno-X kit (Clontech). Briefly, PCR amplificates were cloned directionally into the corresponding sites in the transfer vector, pShuttle (Clontech), under control of the CMV promoter. Clones were DNA sequenced completely. An expression cassette containing the antigen was excised and ligated with the genomic adenoviral plasmid, pAdeno-X (E1 and E3 deleted serotype Ad5). Screening of recombinants from *E. coli* was done by restriction analysis and PCR. Correct clones were then transfected into 293 cells (ATCC) using LipofectAmine Plus reagent (LifeTechnologies). Expression was verified by SDS-PAGE on infected cell lysates using an anti-His Ab. Virus was isolated and high titer stocks were produced as previously described [Spector, 1995].

Antigens

The fusion protein of Ag85B and ESAT-6 (in the following abbreviated to Ag85B-ESAT6) and Ag85B were produced recombinantly as previously described (Olsen et al, 2001). The LPS content was measured by the *Limulus amoebocyte* lysate test and shown to be below 0.125 EU/millilitre—a concentration having no influence on cellular activity. Synthesis of the peptide covering the first 20 amino acids of ESAT-6 (in the following abbreviated $ESAT6_{1-20}$) was performed in a Teflon filter by solid-phase peptide synthesis as previously described (Chang et al, 1978).

The fusion protein of the *Plasmodium falciparum* Glutamate-rich protein and the merozoite surface protein (In the following abbreviated to GLURP-MSP3) was produced as previously described (Theisen et al, 2004).

Ovalbumin (In the following abbreviated to OVA) was purchased at Sigma Aldrich.

Tetanus toxoid and Diphtheria toxoid were purchased from Statens Serum Institut, Copenhagen.

Recombinant major outer membrane protein from *Chlamydia muridarum* (in the following abbreviated MOMP) were expressed in the pDest17 system (Gateway, Invitrogen)

Immunization

Mice were immunized subcutaneously (sc) at the base of the tails three times with a two weeks interval between each immunization. The vaccines (0.2 millilitre/mice) consisted of 1-2 micrograms of the fusion protein Ag85B-ESAT6 emulsified in 250 micrograms DDA and 100 micrograms of either total lipids, or 0.1-100 micrograms purified polar or apolar lipids. Alternatively, the vaccines containing fusion protein was adjuvanted with total lipids alone, 500 micrograms Alhydrogel, or 250 micrograms DDA. As a positive control, a single dose of BCG Danish 1331 was injected sc at the base of the tail. Moreover, fusion protein administered in 250 micrograms DDA and 100 micrograms TDB was included in some experiments for comparison.

For studying adverse effects, 2 micrograms of the fusion protein antigen 85B and ESAT-6 emulsified in 250 micrograms DDA was injected intra-muscularly (i.m.) without or with two different doses of total lipids (a high dose of 250 micrograms as well as a low dose of 20 micrograms). For comparison, a group receiving fusion protein in 70% Montanide ISA720 as well as a control group receiving no immunization was included. All vaccines were injected 3 times in the right and left femur muscle in a volume of 50 microliters in each leg. Tissue sections were prepared and stained with hematoxylin-eosin by IN-Lab Medico A/S operating according to GLP-standard. All tissue sections were examined by a pathologist with no knowledge on the nature of the samples.

Experimental Infections

For evaluation of vaccine efficacy, mice were challenged 10-25 weeks after the first immunisation by the aerosol route in a Glas-Col inhalation exposure system calibrated to deposit approximately 25 CFU of virulent *M. tuberculosis* Erdman in the lungs. The bacterial load in spleen and lungs were determined six weeks later by plating serial dilutions onto Middlebrook 7H11 agar supplemented with 2 μl 2-thiophene-carboxylic acid hydrazide per millilitre to selectively inhibit the growth of BCG. Colonies were counted after 2-3 weeks of incubation at 37° C.

Lymphocyte Cultures

Blood samples were drawn from mice 7 days after the last immunisation, pooled from 5-6 mice in each group and the blood lymphocytes purified on a density gradient. Spleen lymphocytes were obtained as previously described (Andersen et al, 1991). Cell cultures were performed in triplicate in round-bottomed microtiter wells containing $2\times10^5$ cells in a volume of 200 microlitres RPMI supplemented with 2-mercaptoethanol, glutamine, penicillin-streptomycin, hepes, and 10% foetal calf serum. Mycobacterial antigens (Ag85B-ESAT6, Ag85B, $ESAT6_{1-20}$) were used in concentrations ranging from 5 to 0.08 micrograms/millilitre. Wells containing medium only and 5 micrograms/millilitre of ConA were included in all experiments as negative and positive controls, respectively. Culture supernatants were harvested from parallel cultures after 72 hours of incubation in the presence of antigen, and the amount of IFN-gamma was determined by enzyme-linked immunosorbent assay (Brandt et al, 2000).

Fusion Protein Specific IgG Elisa

ELISA plates (Nunc, Maxisorp) were coated with Ag85B-ESAT6, Glurp-MSP3, or OVA (0.05 micrograms/well) overnight at 4° C. Free binding sites were blocked with PBS containing 2% skimmed milk. Pooled mouse sera from 18 mice/group were analysed in duplicate in five-fold dilutions at least ten times in PBS with 1% bovine serum albumin. Total IgG (61-6520, diluted 1/1000, Zymed), IgG1 (), or IgG2a antibody was detected by TMB substrate as described by the manufacturer (Kem-en-tec). Antibody titers are expressed as the midpoint titres.

Statistical Methods

Differences in number of colonies between infected mice and control mice were tested by analysis of variance. When significant effects were indicated, differences between means were assessed by Dunnetts test.

Example 1

TLC of Total, Polar and Apolar Lipids from *M. bovis* BCG

Figure 1:
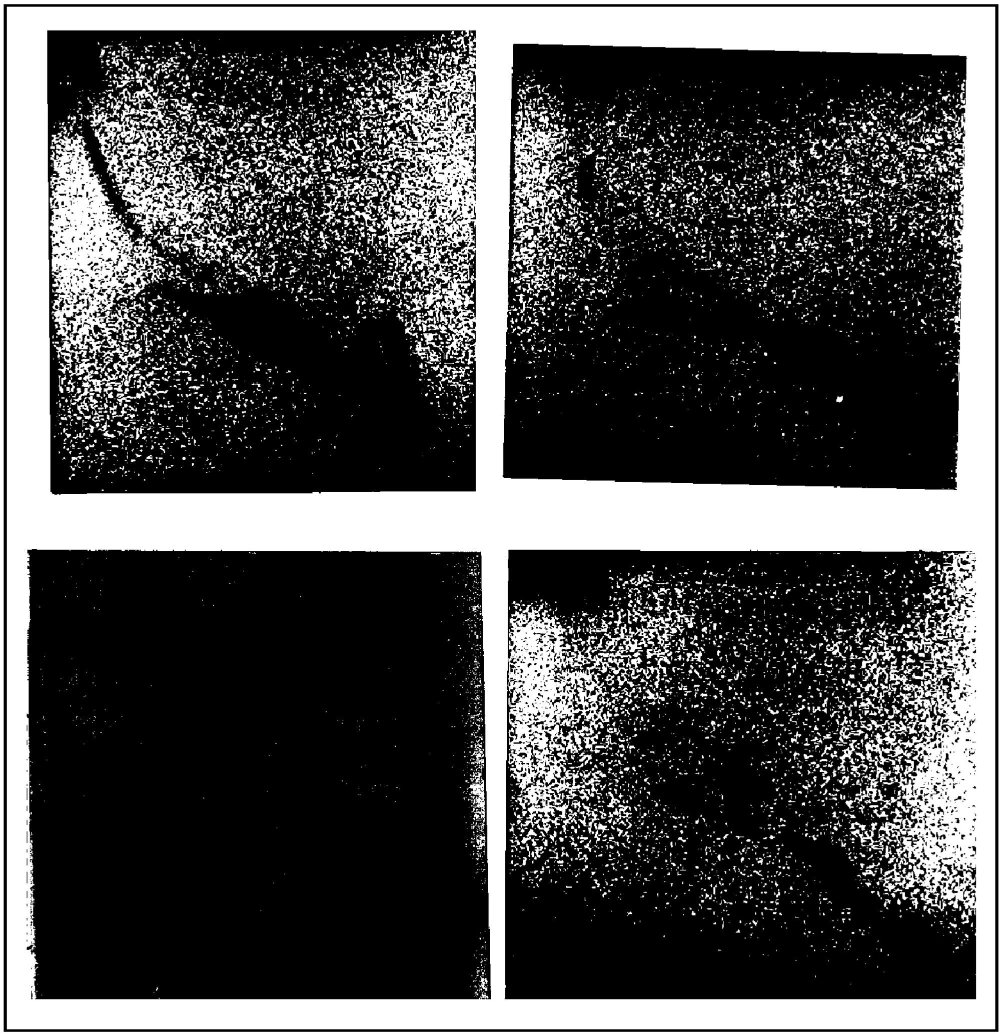

The apolar lipids identified in the total extract were phthiocerol A dimycocerosate (A), phthiocerol C dimycocerosate (C), and a small amount of phthiocerol B dimycocerosate (B). Large, amounts of triacylglycerol (TG) were also detected. These lipids were also detected in the apolar extract as expected. In the polar extract, only a trace of TG and a spot probably representing free fatty acids (FFA) were detected (FIG. 1).

Figure 2:
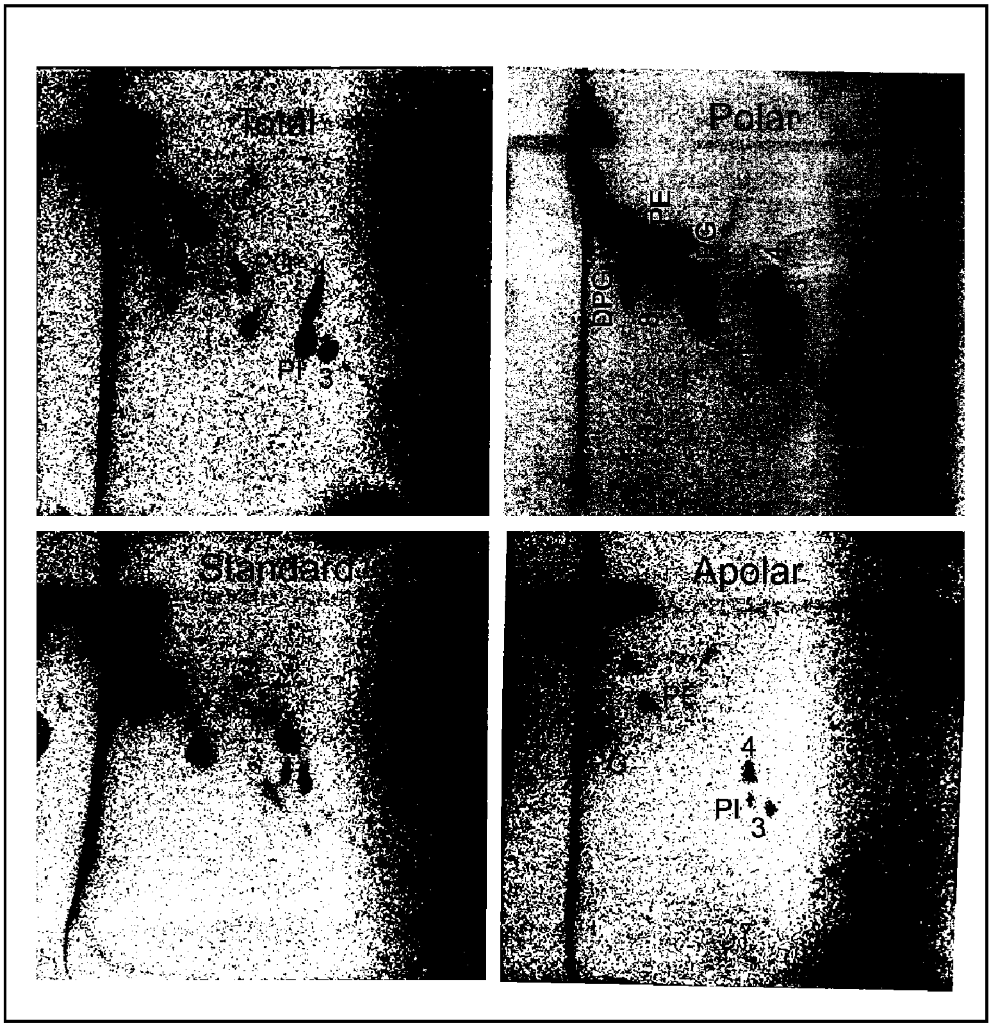

The total and polar extract contained the following polar lipids: Phosphatidylinositol mannosides, probably triacylated (1) and tetracylated (2) pentamannosides, and triacylated (3) and tetracylated (4) dimannosides. Phosphatidylinositol (PI), phosphatidylethanolamine (PE) and diphosphatidylglycerol (cardiolipid, DPG) were major phospholipids. Small amounts of L-alpha-Phosphatidyl-DL-glycerol sodium salt (PG) and another phospholipid (7) were also present. A glycolipid (8) was also observed in the polar extract. Only the more abundant lipids could be detected in small amounts in the apolar extract (FIG. 2).

Figure 3:
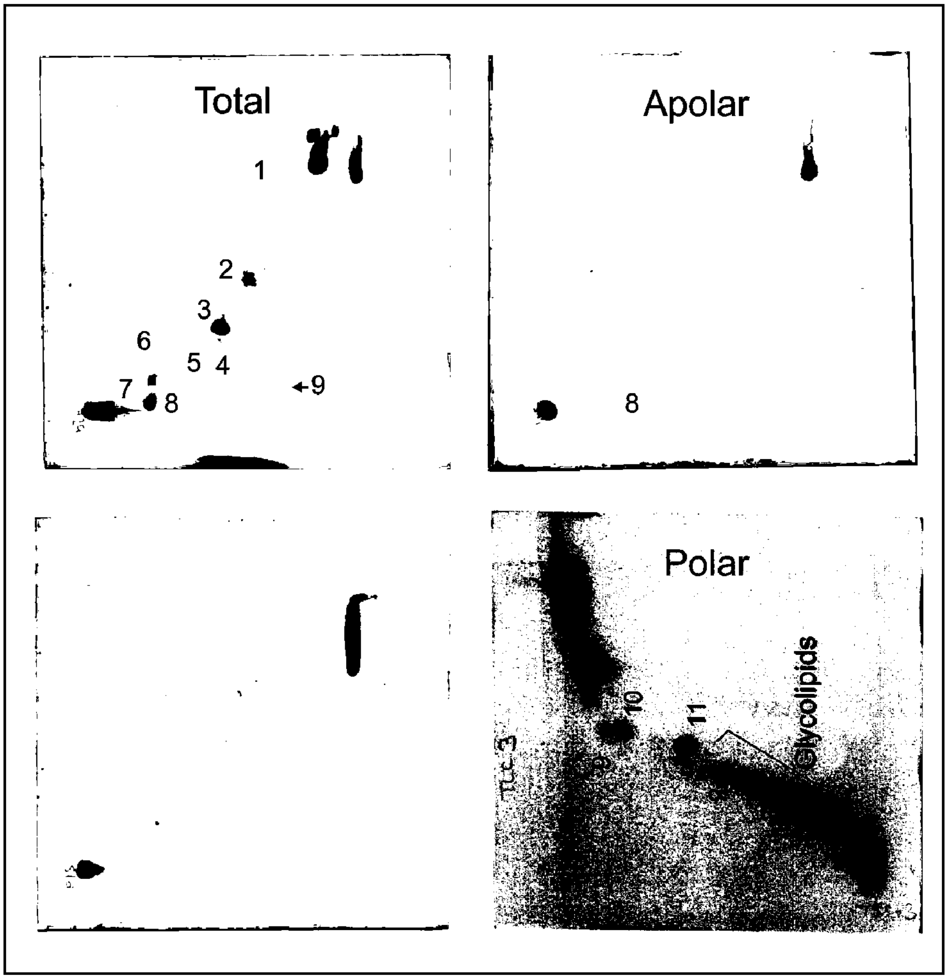

Nine minor glycolipids of intermediate polarity were detected in the total extract (labelled 1-9), one is expected to be "cord factor" trehalose dimycolate, the identity of the other lipids is unknown. Two additional glycolipids (10 and 11) were identified in the polar extract. Relatively small amounts of glycolipids were detected in the apolar and polar extract, respectively (FIG. 3).

Figure 4:
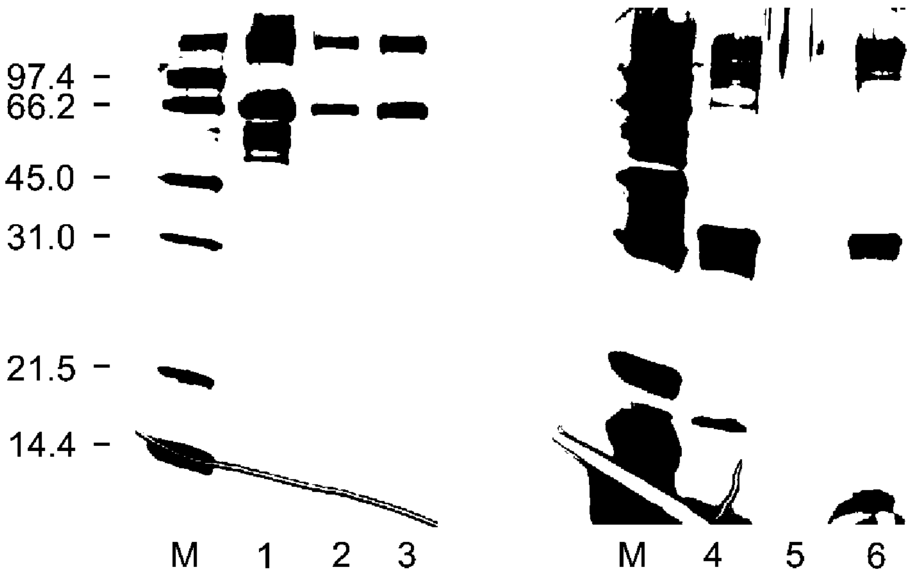

Adsorption of Bovine Serum Albumin and the Recombinant Ag85B-ESAT6 Fusion Protein to the DDA and Total Lipid Adjuvant Two identical tubes were prepared by mixing 0.5 millilitre of the total lipid solution (1 milligrams/millilitre) with antigen: 100 micrograms bovine serum albumin (BSA) or 50 micrograms of Ag85B-ESAT6. Thereafter, 0.5 millilitre of the DDA solution was added to the lipid/antigen mixture. Adsorption was allowed to proceed over night. To study the amount of antigen bound to DDA/lipid, the vaccine preparations were ultracentrifuged (100,000 g, 1 hour). From the first tube, the supernatant was collected and the pellet was resuspended in the original volume (1 millilitre) and analysed by SDS-PAGE (FIG. 4). From the second tube, the supernatant was removed and the pellet was washed with 2 millilitres of distilled water followed by ultracentrifugation (100,000 g, 1 hour). The supernatant and the pellet resuspended in 1 millilitre was analysed by SDS-PAGE (FIG. 4). Most of the BSA and Ag85B-ESAT6 antigen is found in the adjuvant pellet (lane 3, 6), whereas only limited amounts were observed in the supernatants (lane 2, 5), indicating that the majority of antigen is adsorbed to the adjuvant fraction.

Example 2

Use of Total Lipids from *M. bovis* BCG for Immunization of Mice

In this example studying the adjuvant activity of *M. bovis* BCG total lipids, mice were immunized with experimental vaccines consisting of 1 microgram of fusion protein Ag85B-ESAT6 emulsified in DDA adjuvanted with 100 µg of total lipids. Groups of mice receiving the Ag85B-ESAT6 alone, the Ag85B-ESAT6 and DDA alone, the Ag85B-ESAT6 in combination with the total lipids and a group of naïve mice was included as negative controls, while Ag85B-ESAT6/DDA/TDB and a standard BCG vaccine were included as positive controls. This experiment was carried out using Th2 prone Balb/C mice (Peltoniemi et al, 2002), as only remarkably potent Th1-inducing adjuvants are capable of switching the immune response of this mouse strain in favour of a response characterized by production of Th1 cytokines such as IFN-gamma.

Figure 5:
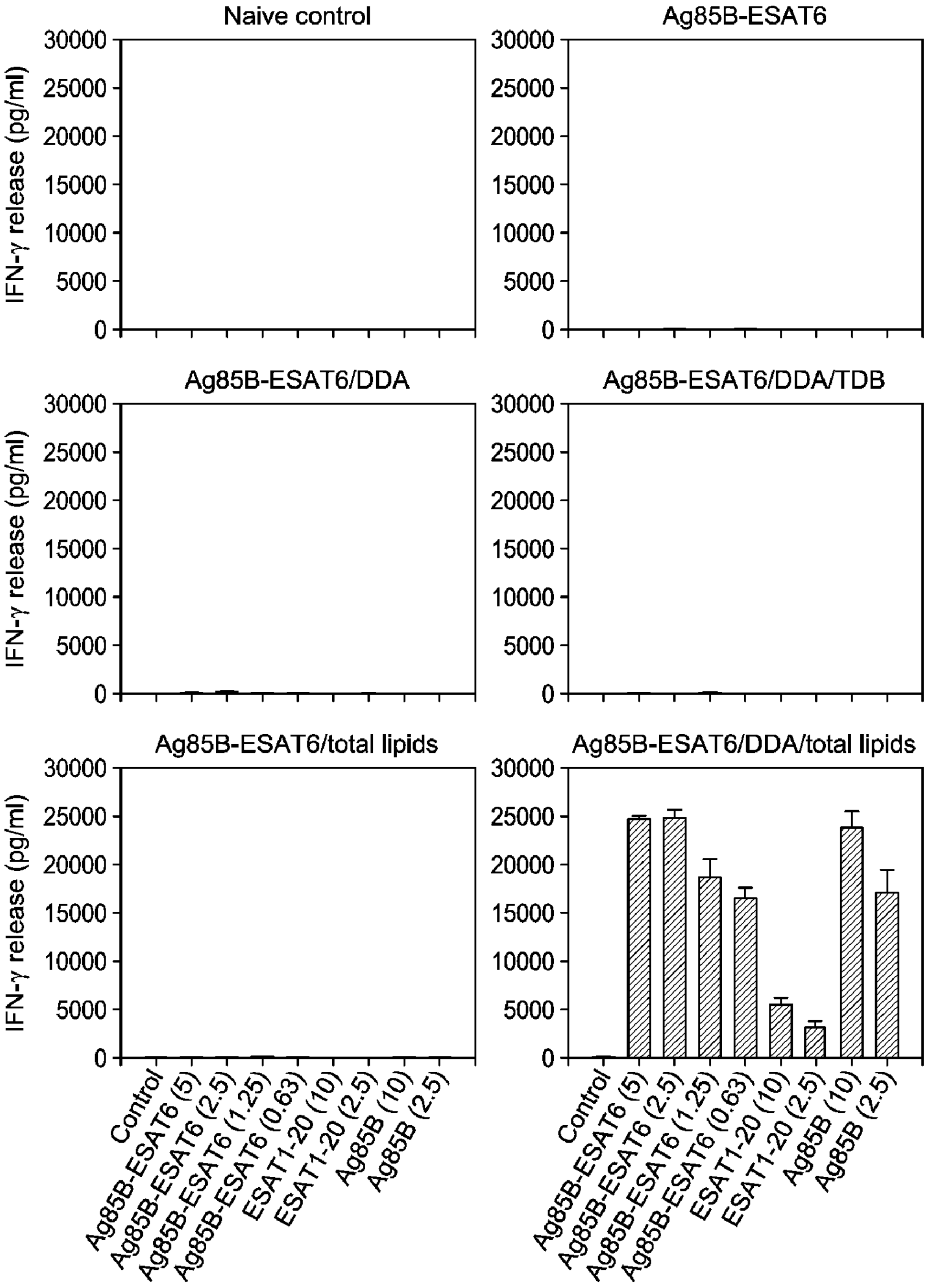

Five weeks after the first immunization, the IFN-gamma release was evaluated after in vitro re-stimulation of blood lymphocytes with different concentrations of Ag85B-ESAT6, Ag85B, and the dominant ESAT6 peptide ($ESAT6_{1-20}$) covering the first 20 amino acids of the ESAT6 protein (Brandt et al, 2000). Only the group of mice vaccinated with Ag85B-ESAT6/DDA/total lipids gave a prominent response to Ag85B-ESAT6, Ag85B and $ESAT6_{1-20}$ in the Balb/C mice (FIG. 5). No IFN-gamma release was seen after vaccination with Ag85B-ESAT6 in DDA alone or in DDA/TDB in this mouse strain in contrast to the marked IFN-gamma secretion seen in the Th1-prone C57B1/6 mice (Brandt et al, 2000, Holten-Andersen et al, 2004).

To evaluate the level of protection, mice were challenged 10 weeks after the first immunization by the aerosol route. Protective efficacies are expressed as the $\log_{10}$ reduction in bacterial counts in immunized mice in comparison with a group of un-immunized naïve animals (Table 1). The results presented in Table 1 demonstrate that Ag85B-ESAT6/DDA/total lipids was the only subunit vaccine to induce levels of protection comparable to BCG. The combination of DDA/total lipids gave rise to significantly superior protection in the spleen compared to total lipids alone ($p<0.001$). Moreover, the protection obtained with DDA/total lipids as the adjuvant formulation was remarkably better than DDA ($p<0.05$) although this adjuvant previously has been shown to provide protection at the level of BCG in the C57B1 mouse strain (Brandt et al, 2000).

TABLE 1

Vaccine-induced protection in the mouse model[a].

| VACCINE[B] | LUNGS $Log_{10}$ resistance ± SEM | SPLEEN $Log_{10}$ resistance ± SEM |
|---|---|---|
| Ag85B-ESAT6 | 0.01 ± 0.08 | 0.14 ± 0.08 |
| Ag85B-ESAT6/DDA | 0.09 ± 0.15 | 0.28 ± 0.10 |
| Ag85B-ESAT6/DDA/TDB | 0.53 ± 0.17 | 0.36 ± 0.19 |
| Total lipids | 0.32 ± 0.07 | 0.29 ± 0.10 |
| Ag85B-ESAT6/total lipids | 0.48 ± 0.08 | 0.47 ± 0.16 |
| Ag85B-ESAT6/DDA/total lipids | 1.19 ± 0.13 | 0.97 ± 0.18 |
| BCG | 1.10 ± 0.17 | 1.30 ± 0.25 |

[a]The protective efficacies of vaccines are expressed as the $\log_{10}$ reduction of the bacterial load ($\log_{10}$ resistance).

[B]Mice (n = 6) were given a BCG vaccination or immunized s.c. with the indicated experimental vaccines.

For comparison, C57B1/6 mice were immunized with Ag85B-ESAT6 in DDA/total lipids as well as DDA/TDB and blood lymphocytes re-stimulated in vitro as above (FIG. 6). In this mouse strain, the two adjuvant formulations give rise to comparable levels of immune responses. Together these results demonstrate that although both adjuvant formulations give rise to prominent Th1 responses characterized by the secretion of high amounts of IFN-gamma in the Th1 prone C57B1 mice, only the most remarkably Th1 adjuvant, the combination of DDA/total lipids, are capable of inducing a IFN-gamma responses in Th2 prone Balb/C mice.

The Longevity of Immunity Induced by *M. bovis* BCG Lipid Extract

A waning of the immune response generated by adjuvanted subunit vaccines has been mentioned as one of the major drawbacks of this vaccine technology. In order to study the longevity of the immunity provided by DDA/total lipids, C57B1/6 mice were immunized three times with Ag85B-ESAT6/DDA/total lipids and immune responses measured at two different time points after the first immunisation. Spleens were isolated 6 and 13 months after the first immunization and lymphocytes restimulated in vitro with various concentrations of Ag85B-ESAT6 as well as Ag85B and $ESAT6_{1-20}$. For comparison, mice immunized with Ag85B-ESAT6 in DDA/TDB as well as a vaccine based on a priming with Ag85B-ESAT6 in DDA/TDB followed by two immunizations with a non-replicating adenovirus vaccine expressing Ag85B-ESAT6 were included. In particularly, mice immunized with DDA/total lipids give rise to sustained immune responses as shown in FIG. 7. Six months after the first immunization, the group receiving DDA/total lipids show IFN-gamma responses three times as high as mice receiving the two other vaccine constructs and even as late as 13 month after immunization, IFN-gamma levels are twice as high in the DDA/total lipid group.

Figure 8A:
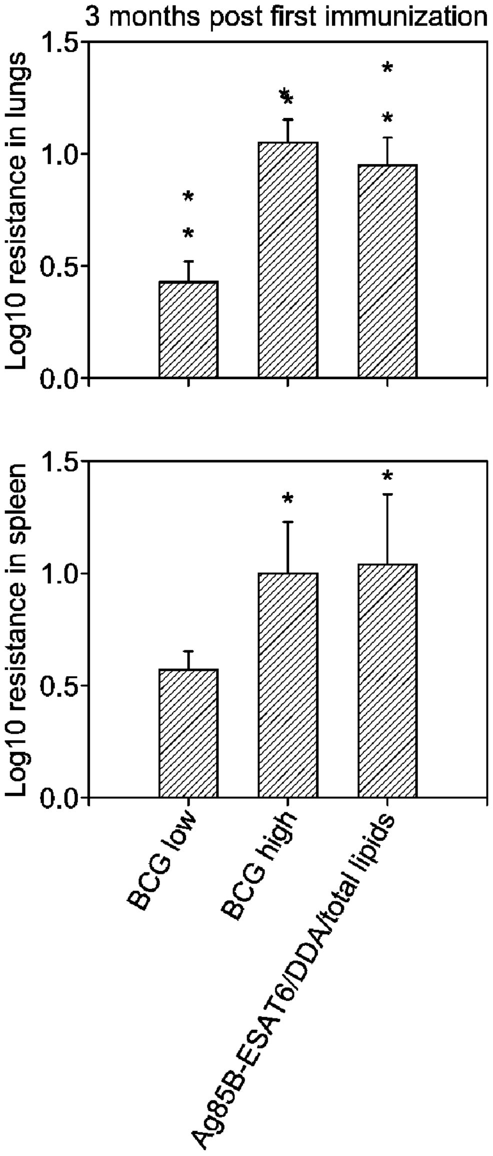
Figure 8B:
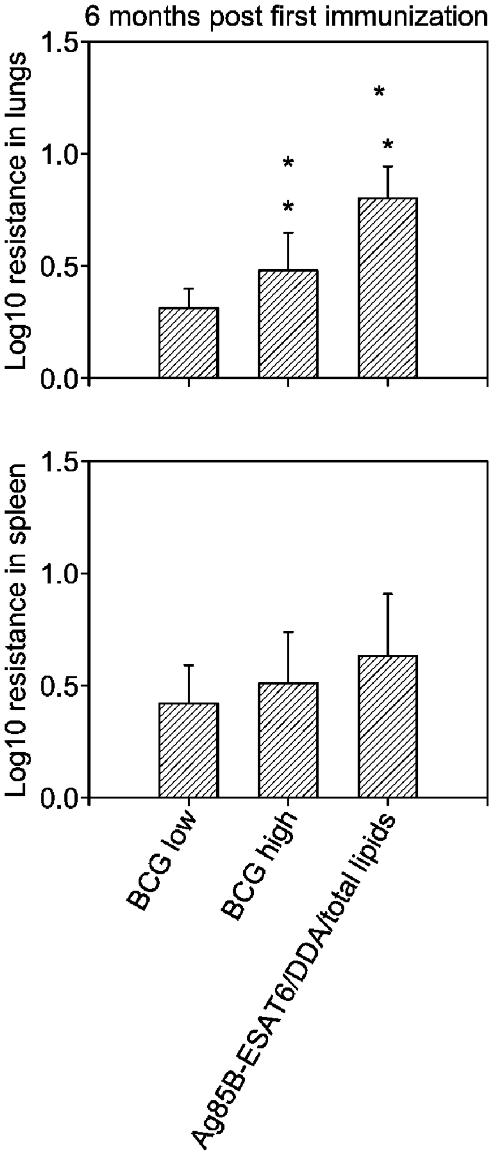

The protective efficacy of Ag85B-ESAT6/DDA/total lipids after an aerosol challenge was tested 3 and 6 months post first immunization and compared to that of two different doses of the standard BCG vaccine. At the early time point (3 months), the high dose of BCG and the subunit vaccine gave rise to significant levels of protection in both organs (FIG. 8, panel A). Although the standard BCG vaccine is a live vaccine, which should provide superior long-term protection, vaccination with the Ag85B-ESAT6/DDA/total lipids resulted in sustained immune responses giving rise to protective levels comparable to the high dose of BCG at this late time point (FIG. 8, panel B). Compared to the low dose of BCG, Ag85B-ESAT6/DDA/total lipids gives significantly higher levels of protection in the lungs ($p<0.05$). These data demonstrates that Ag85B-ESAT6/DDA/total lipids is inducing stable immunological memory superior to that induced by the low dose of the current human vaccine.

Induction of Humoral Activity with *M. bovis* BCG Total Lipids

Although antibodies are not known to play an important role in immunity to *M. tuberculosis*, it can still serve as a useful marker of immunogenicity. The ability of DDA/total lipids to generate humoral activity was therefore investigated by monitoring the Ag85B-ESAT6 specific IgG antibody response five weeks after the first immunization. For comparison, an aluminium-based adjuvant (Alhydrogel) and DDA alone were included. As shown in table 2, high titers of specific IgG were present in sera from mice vaccinated with Ag85B-ESAT6 in DDA/total lipids. Compared with titers obtained after immunization with Ag85B-ESAT6/DDA or Ag85B-ESAT6/Alhydrogel, the optimized adjuvant formulation comprising total lipids induced higher level of specific antibodies.

TABLE 2

Antigen-specific antibody midpoint titres in serum from Ag85B-ESAT6 immunised Balb/c mice

| | Total IgG[a] |
|---|---|
| Naïve control | <100 |
| BCG | <100 |
| Ag85B-ESAT6/Alhydrogel | 1100 |
| Ag85B-ESAT6/DDA | 1540 |
| Ag85B-ESAT6/DDA/total lipid | 2200 |

[a]Ag85B-ESAT6 specific IgG levels 5 weeks after the first immunization as measured by ELISA.

Adverse Effects of Vaccination with BCG Total Lipids and DDA

Two different doses of total lipids (a high dose of 250 micrograms as well as a low dose of 20 micrograms) in combination with 250 micrograms of DDA were administered i.m. in Balb/C mice three times with a two weeks interval between each immunisation. For comparison, a group receiving no immunization, 250 micrograms DDA alone, or 70% Montanide was also included. Montanide is already approved for clinical trials in humans and has been used extensively in clinical trials since late 1990s.

The grade of inflammation or reaction in the muscle tissue and the surrounding adipose tissue was quantified and the number of plasmacells, lymphocytes, macrophages, and neutrophil granulocytes was determined (Table 3). The following parameters have been used:

1. Inflammation in muscle tissue (grade 0 is no inflammation, grade 1 is mild inflammation, grade 2 is moderate inflammation, grade 3 is heavy inflammation)
2. Inflammation in adipose tissue (grade 0 is no inflammation, grade 1 is mild inflammation, grade 2 is moderate inflammation, grade 3 is heavy inflammation)
3. The amount of necrotic adipose tissue (grade 0 is no necrosis, grade 1 is small necrotic areas, grade 2 is some necrosis, grade 3 is large areas with necrosis)
4. The number of plasma cells (grade 0 is no plasma cells, grade 1 is a few plasma cells, grade 2 is a moderate number of plasma cells, grade 3 is a high number of plasma cells)
5. The number of lymphocytes (grade 0 is no lymphocytes, grade 1 is a few lymphocytes, grade 2 is a moderate number of lymphocytes, grade 3 is a high number of lymphocytes)
6. The number of macrophages (grade 0 is no macrophages, grade 1 is a few macrophages, grade 2 is a moderate number of macrophages, grade 3 is a high number of macrophages)
7. The number of neutrophil granulocytes (grade 0 is no granulocytes, grade 1 is a few granulocytes, grade 2 is a moderate number of granulocytes, grade 3 is a high number of granulocytes)

TABLE 3

Effects in tissue after immunization with different adjuvants

| | 1 | 2 | 3 | 4 | 5 | 6 | 7 |
|---|---|---|---|---|---|---|---|
| Control | 0 | 0 | 0 | 0 | 0 | 0 | 0 |
| 250 μg DDA | 0 | 3 | 0 | 1-1.5 | 1-1.5 | 3 | 1-1.5 |
| 250 μg DDA/ 20 μg total lipids | 0 | 2-2.5 | 0 | 1-1.5 | 1-1.5 | 3 | 1-1.5 |
| 250 μg DDA/ 250 μg total lipids | 0 | 3 | 0 | 1-1.5 | 1-1.5 | 3 | 1-1.5 |
| Montanide ISA 720 | 2-2.5 | 3 | 3 | 2-2.5 | 1-1.5 | 3 | 2-2.5 |

In vaccines containing DDA, one or more small foci with inflammatory activity were seen in the adipose tissue. This inflammation was characterized by a large increase in the number of macrophages particularly in the vicinity of lymph-nodes. There was no effect of adding total lipids demonstrating that despite the potent adjuvant activity, total lipids has no additive effect on adverse reactions.

In contrast, injection with Montanide ISA 720 also results in severe inflammation in the muscles and large areas with necrosis in the adipose tissue. This relative higher level of adverse effects is also reflected in the increased number of plasma cells and neutrophil granulocytes.

The Dose Range of BCG Total Lipids and DDA

Various doses of total lipids (see table 4 and 5) were administered with 250 micrograms of DDA s.c. in Balb/C as well as C57B1 mice three times as previously described to determine the optimal ratio of the total lipids. Immune responses were monitored in the blood 5 and 7 weeks after the last immunization by re-stimulation in vitro with 5 microgram/millilitres of Ag85B-ESAT6.

TABLE 4

Dosis-response of total lipids/DDA in Balb/C mice

| Emulsion | Total lipids (micrograms) | DDA (micrograms) | Immune response[a] | Immune response[b] |
|---|---|---|---|---|
| 1 | 250 | 250 | 469 ± 164 | 288 ± 265 |
| 2 | 100 | 250 | 1328 ± 216 | 1194 ± 15 |
| 3 | 20 | 250 | 6319 ± 317 | 217 ± 156 |
| 4 | 5 | 250 | 181 ± 113 | 101 ± 102 |
| 5 | 1 | 250 | 254 ± 191 | 163 ± 6 |
| 6 | 0 | 250 | 128 ± 17 | 0 ± 0 |

[a]Release of IFN-gamma from blood lymphocytes isolated 5 weeks after the first immunization.
[b]Release of IFN-gamma from blood lymphocytes isolated 7 weeks after the first immunization.

TABLE 5

Dosis-response of total lipids/DDA in C57BL/6 mice

| Emulsion | Total lipids (micrograms) | DDA (micrograms) | Immune responses[a] |
|---|---|---|---|
| 1 | 250 | 250 | 57436 ± 3703 |
| 2 | 100 | 250 | 48403 ± 5069 |
| 3 | 20 | 250 | 1421 ± 197 |
| 4 | 5 | 250 | 2206 ± 256 |
| 5 | 1 | 250 | 2376 ± 967 |
| 6 | 0 | 250 | 881 ± 257 |

[a]Release of IFN-gamma from blood lymphocytes isolated 5 weeks after the first immunization.

The highest immune response was observed in the range of 20-100 micrograms of total lipids, and 100 micrograms of total lipid was thereafter used in combination with the standard dose of 250 micrograms of DDA.

Evaluation of Total Lipids/DDA as an Adjuvant for Different Antigens

That total lipids/DDA can enhance immune responses not only to a TB antigen but also to antigens from other sources was tested by immunizing with 5 micrograms of the Ag85B-ESAT6 fusion as well as a hybrid molecule consisting of the GLURP and the MSP-3 of *Plasmodium falciparum* and 5 micrograms of ovalbumin. In addition, MOMP, tetanus toxoid, and diphtheria toxoid were also included for immunisation. All antigens were emulsified in 100 micrograms of total lipids/250 micrograms of DDA and administered three times by the s.c. route. Immune responses were monitored 5 weeks after the first immunization (Table 6 and 6A).

TABLE 6

The ability of total lipids/DDA to enhance immune responses of antigens from various sources, expt. 1

| Antigen | IgG1[a] | IgG2a[b] | Immune response[c] |
|---|---|---|---|
| Ag85B-ESAT6 | 6670 | 250 | 10116 ± 109 |
| Glurp-MSP3 | 670 | <100 | 1112 ± 365 |
| OVA | 2500 | <100 | 793 ± 81 |
| No antigen[d] | | | 119 ± 6 |

[a]Antigen-specific IgG1 levels (midpoint titres) 5 weeks after the first immunization as measured by ELISA.
[b]Antigen-specific IgG2a levels (midpoint titres) 5 weeks after the first immunization as measured by ELISA.
[c]Release of IFN-gamma from blood lymphocytes isolated 5 weeks after the first immunization and re-stimulated in vitro with the relevant antigen in a dose of 5 microgram/millilitres.
[d]Blood lymphocytes from un-immunized mice stimulated with the no antigen.

TABLE 6A

The ability of total lipids/DDA to induce immune responses of antigens from various sources, expt. 2

| Antigen | Immune response[a] |
|---|---|
| Ag85B-ESAT6 | 72600 ± 12600 |
| MOMP | 168000 ± 6230 |
| Tetanus toxoid | 52500 ± 13500 |
| Diphteria toxoid | 29000 ± 6600 |
| No antigen[b] | 460 ± 300 |

[a]Release of IFN-gamma from blood lymphocytes isolated 5 weeks after the first immunization and re-stimulated in vitro with the relevant antigen in a dose of 5 microgram/millilitres.
[b]Blood lymphocytes from un-immunized mice stimulated with the no antigen.

These results demonstrate that total lipids/DDA is capable of inducing an immune response measured as increased levels of antigen-specific antibodies and/or IFN-gamma when used in combination with antigens from different sources as shown in table 6 and 6A. This emphasizes that total lipids/DDA can be used as an adjuvant formulation not only for TB vaccines but also for infectious diseases, allergy, autoimmune diseases or cancer.

Evaluation of Different Liposome Forming Compounds

The ability of different cationic reagents to enhance immune responses of total lipids was monitored in Balb/C mice. Also, a neutral liposome preparation (consisting of PC and DOPE), anionic liposomes (PC, DOPE, and PG), and a group of naïve un-immunized mice were included for comparison. All vaccines contained 250 micrograms of liposomes and were given s.c. in combination with 100 micrograms of total lipids and as vaccine antigen, two micrograms of the fusion-protein Ag85B-ESAT6 was used. As above, immune responses were monitored 5 weeks after the first immunization by in vitro re-stimulation of blood lymphocytes with different concentrations of Ag85B-ESAT6.

Figure 9:
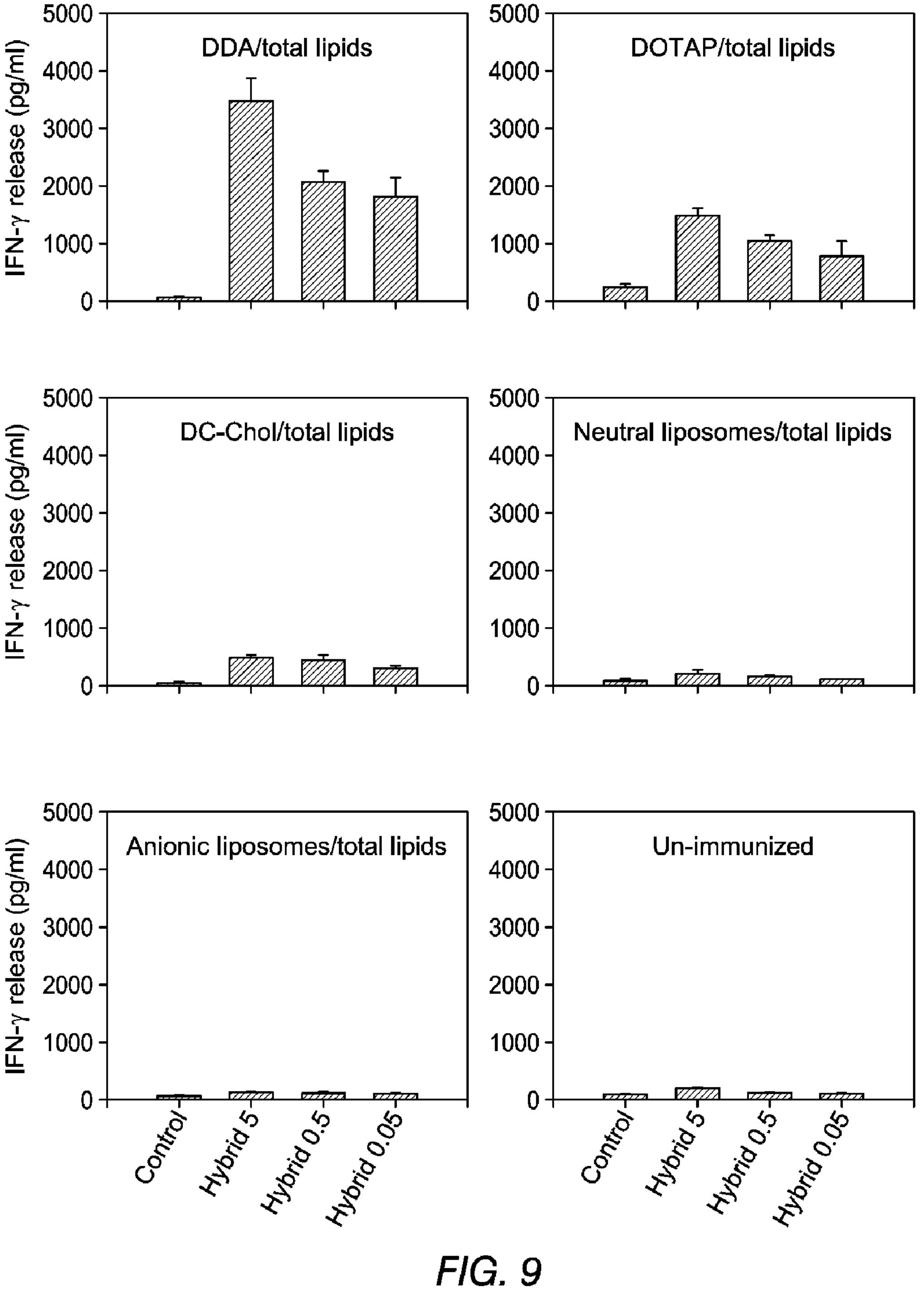

As shown in FIG. 9, total lipids administered with cationic surfactants such as DDA, DOTAP, and DC-Chol give rise to high levels of IFN-gamma. In particular, the combination of total lipids/DDA induced substantial IFN-gamma production.

Figure 10:
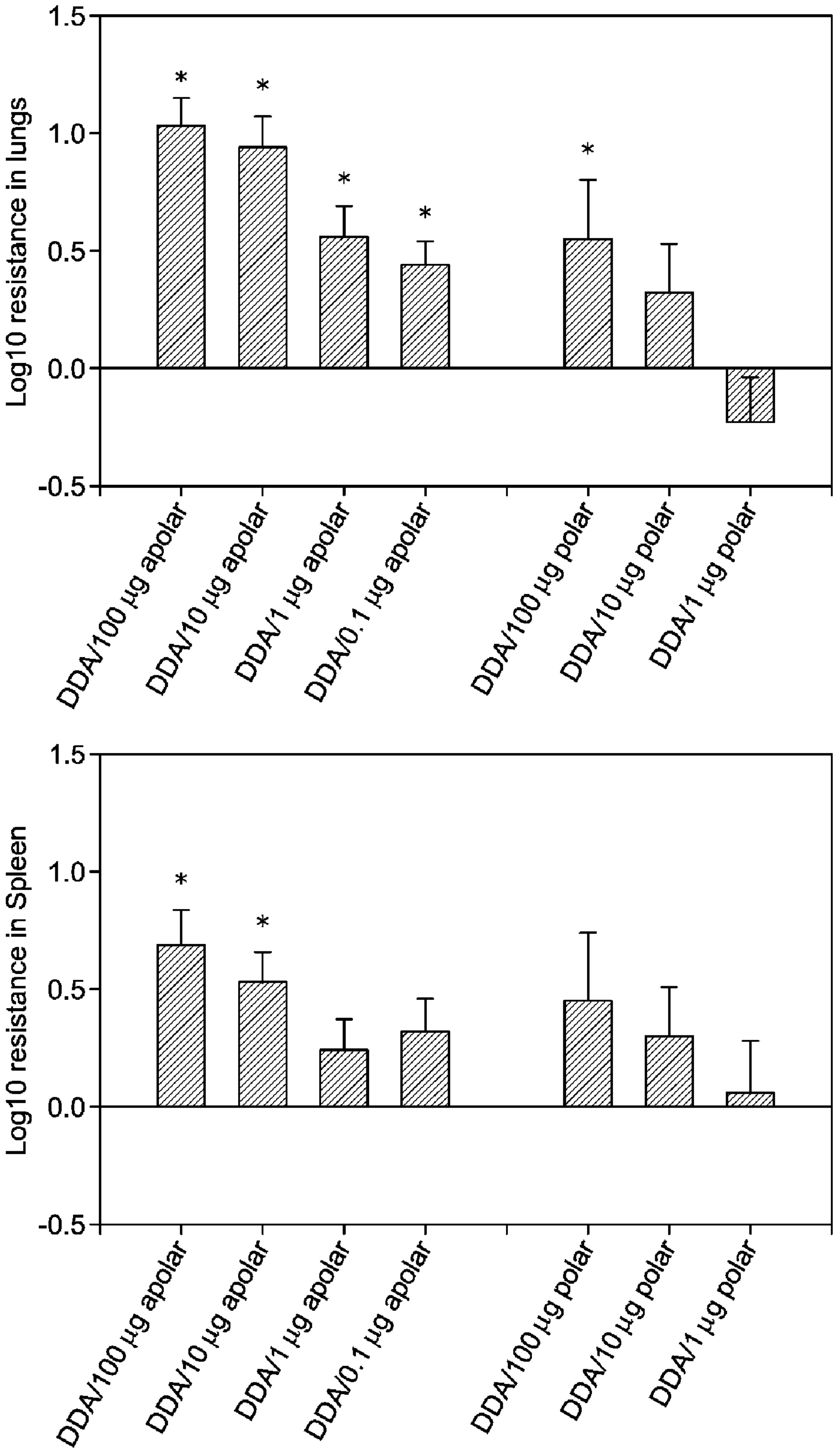

Immunological Properties of Apolar and Polar Lipids Purified from *M. bovis* BCG Total Lipid Extract To perform a more detailed characterisation of the stimulatory lipids responsible for the pronounced immune responses seen after vaccination with DDA/total lipids, apolar and polar lipids were purified from BCG total lipid extract and tested in various different concentrations together with 250 micrograms DDA as vaccine adjuvants. Mice were immunized with the adjuvants in combination with 2 micrograms of Ag85B-ESAT6. As shown in FIG. 10, immunization with Ag85B-ESAT6/DDA/apolar lipids resulted in significant reduction in number of bacteria in the lungs even with a dose as low as 0.1 microgram apolar lipids. Although the high dose of polar lipids in combination with DDA gave rise to significant protection in the lungs, lower protective levels were in general obtained using vaccine based on the polar lipids indicating that the majority of components with adjuvant activity are located in the apolar lipid fraction.

A preparation of extractable total polar lipids of *Mycobacterium bovis* BCG was previously found to promote immune responses to antigen in mice (Sprott WO 03/011336). In order to compare with total lipids, polar, and apolar lipids described in this study, a preparation of chloroform soluble extractable total polar lipids was prepared according to the protocol of Sprott et al. 50 micrograms of these preparations were used for immunization of Balb/C mice with or without the addition of 250 microgram of DDA. The fusion protein of Ag85B-ESAT6 was used as the vaccine antigen in a dose of 2 microgram. Immune responses measured as IFN-γ release were evaluated in the blood five weeks after the first immunisation by re-stimulation with medium only (control) or 5 microgram/millilitres of Ag85B-ESAT6 (Table 7). Also the fusion protein specific antibody mid-titres was determined in the serum of mice vaccinated 5 weeks previously (Table 8).

TABLE 7

| Immunogenicity of various polar, apolar, and total lipid extracts. | | |
|---|---|---|
| VACCINE[B] | IFN-γ release (pg/m1) ± SEM[a] Control | IFN-γ release (pg/ml) ± SEM[a] Ag85B-ESAT6 (5 μg/ml) |
| DDA/Total lipids | 19 ± 5 | 1194 ± 26* |
| Apolar lipids | 6 ± 2 | 26 ± 11 |
| DDA/apolar lipids | 37 ± 9 | 4516 ± 33* |

TABLE 7-continued

Immunogenicity of various polar, apolar, and total lipid extracts.

| VACCINE[B] | IFN-γ release (pg/ml) ± SEM[a] Control | IFN-γ release (pg/ml) ± SEM[a] Ag85B-ESAT6 (5 μg/ml) |
|---|---|---|
| Polar lipids | 0 ± 0 | 96 ± 43 |
| Polar lipids/DDA | 19 ± 5 | 745 ± 137* |
| Polar lipids (WO 03/011336) | 21 ± 3 | 145 ± 20 |
| Polar lipids ( WO 03/011336)/ DDA | 7 ± 3 | 28 ± 3 |
| Naive | 30 ± 10 | 36 ± 13 |

[a]IFN-gamma was measured after re-stimulated with medium only (control) or Ag85B-ESAT6 by ELISA.

*Significant different from naïve un-immunized mice determined by Dunnetts method ($p < 0.05$).

TABLE 8

Antigen-specific antibody midpoint titres in serum from Balb/C mice immunised with various polar, apolar, and total lipid extracts.

| | IgG1[a] | IgG2a[b] |
|---|---|---|
| DDA/Total lipids | 1,000 | 286 |
| Apolar lipids | <100 | <100 |
| DDA/apolar lipids | 1,250 | 250 |
| Polar lipids | 155 | <100 |
| Polar lipids/DDA | 20,000 | 500 |
| Polar lipids (WO 03/011336) | <100 | <100 |
| Polar lipids (WO 03/011336)/DDA | 4,000 | 333 |
| Naïve | <100 | <100 |

[a]Antigen-specific IgG1 levels (midpoint titres) 5 weeks after the first immunization as measured by ELISA.

[b]Antigen-specific IgG2a levels (midpoint titres) 5 weeks after the first immunization as measured by ELISA.

As shown in table 7, the combination of DDA/apolar lipids gives rise to the most prominent immune response with high levels of IFN-γ release. Also immunization with DDA/total lipids as well as DDA/polar lipids results in significant IFN-γ production. In contrast, polar lipids made according to the protocol of Sprott et al. fail to elicit IFN-γ above controls levels and no enhancement of the immune response is seen with the addition of DDA. In contrast, the polar lipids in combination with DDA gave rise to high levels of antibody titres (Table 8) suggesting that these preparations give rise to a different immunological response characterised by enhanced antibody levels but with limited ability to induce IFN-gamma release. This pronounced antibody production was particularly observed in the group of mice immunised with DDA and the polar lipids prepared as described in this study. Together, these results demonstrate the unique stimulatory activity of the combination of DDA administered with total lipids, apolar, and polar lipids described in this study.

Optimisation of the Method for Preparing the DDA/Total Lipid Adjuvant

The BCG total lipids containing DDA vesicles were made using the thin lipid film method (Bangham et al 1965). DDA and total lipids were dissolved separately in chloroform methanol (9:1) to a concentration of 10 mg/ml. Specified volumes of each individual compound were mixed in glass test tubes corresponding to the ratios 250 micrograms of DDA and 50 micrograms of total lipids or 250 micrograms of DDA and 100 micrograms of total lipids. The solvent was evaporated using a gentle stream of $N_2$ and the lipid films were dried overnight under low pressure to remove trace amounts of solvent. The dried lipid films were hydrated in Tris-buffer (10 mM, pH=7.4) and placed on a 70° C. water bath for 20 min, the samples were vigorously shaken every 5 min. The prepared DDA/total lipids liposomes were homogenous and could be stored at 4° C. with no change in visual appearance.

Figure 11:
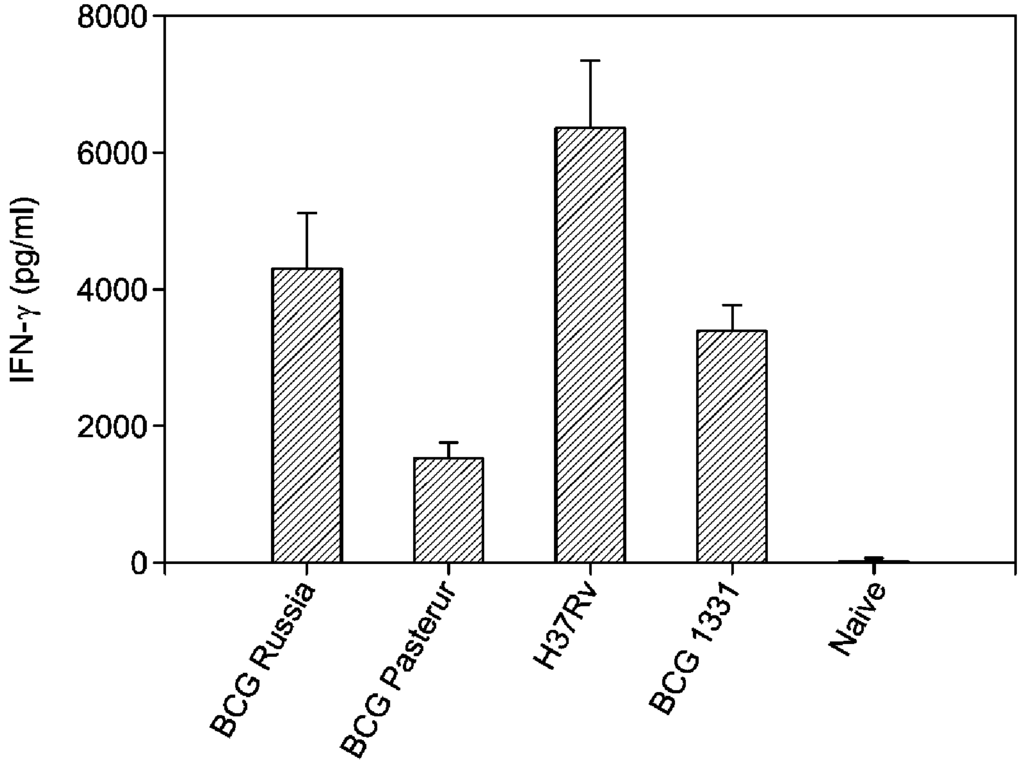

The Immune Response after Immunisation with DDA/Total Lipids from Different Mycobacterial Species Total lipids extracted from *M. bovis* BCG Russia, BCG Pasteur, *M. tuberculosis* H37RV, and BCG 1331 were administered with 250 micrograms of DDA and 2 micrograms of Ag85B-ESAT6 s.c. in Balb/C three times as previously described. Immune responses were monitored in the spleen lymphocytes 5 weeks after the last immunization by re-stimulation in vitro with 5 microgram/millilitres of Ag85B-ESAT6 (FIG. 11). These results clearly demonstrate the unique stimulatory activity of the combination of DDA administered with total lipids is not limited to BCG 1331, but is also observed in other BCG strains as well as the virulent strain *M. tuberculosis* H37Rv.

FIGURE LEGENDS

FIG. 1. 2-D TLC analysis of apolar lipids of *M. bovis* BCG apolar, polar and total lipid extracts.

FIG. 2. 2-D TLC analysis of polar lipids of *M. bovis* BCG apolar, polar and total lipid extracts.

FIG. 3. 2-D TLC analysis of glycolipids of intermediate polarity of *M. bovis* BCG apolar, polar and total lipid extracts.

FIG. 4. Antigen adsorption. Silver stained SDS-PAGE gel of M: Marker proteins. 1: 5 μl BSA, 100 micrograms/millilitres. 2: 5 μl BSA/DDA/Total lipid supernatant. 3: 5 μl redissolved BSA/DDA/Total lipid pellet. 4: 5 μl AG85B-ESAT6, 50 micrograms/millilitres. 5: 5 μl AG85B-ESAT6/DDA/Total lipid supernatant. 6: 5 μl redissolved AG85B-ESAT6/DDA/Total lipid pellet.

FIG. 5. Release of IFN-gamma from blood lymphocytes isolated from naïve Balb/C mice or Balb/C mice immunized with Ag85B-ESAT6, Ag85B-ESAT6/DDA, Ag85B-ESAT6/DDA/TDB, Ag85B-ESAT6/total lipids or Ag85B-ESAT6/DDA/total lipids. Blood samples were drawn 5 weeks after the first immunization, and the lymphocytes were stimulated with no antigen (control), Ag85B-ESAT6 (5, 2.5, 1.25 or 0.63 micrograms/millilitres), Ag85B (10 and 2.5 micrograms/millilitres), and $ESAT6_{1-20}$ (10 and 2.5 micrograms/millilitres).

FIG. 6. Release of IFN-gamma from blood lymphocytes isolated from C57BL mice immunized with Ag85B-ESAT6/DDA/total lipids and Ag85B-ESAT6/DDA/TDB. Blood samples were drawn 5 weeks after the first immunization, and the lymphocytes were stimulated with no antigen (control), Ag85B-ESAT6 (5 micrograms/millilitres), Ag85B (5 micrograms/millilitres), and $ESAT6_{1-20}$ (5 micrograms/millilitres).

FIG. 7. Release of IFN-gamma from splenocytes recovered from mice immunized with Ag85B-ESAT6/DDA/total lipids, Ag85B-ESAT6/DDA/TDB, or one immunization with Ag85B-ESAT6/DDA/TDB followed by two immunizations with Ag85B-ESAT6 in an adenovirus construct. Splenocytes were isolated 6 months (panel A) and 13 months (panel B) after the first immunization and restimulated in vitro with no antigen (control), Ag85B-ESAT6 (5, 1.25, 0.31 micrograms/millilitres), Ag85B (5 micrograms/millilitres), and $ESAT\text{-}6_{1-20}$ (5 micrograms/millilitres).

FIG. 8. $Log_{10}$ resistance in the lungs and spleen of mice (n=5-6) immunized 3 months (panel A) or 6 months (panel B) previously with Ag85B-ESAT6/DDA/total lipids, or two different doses of BCG. * Vaccines inducing significant protection compared to naïve, un-immunized mice ($p<0.05$).

FIG. 9. Release of IFN-gamma from blood lymphocytes isolated from mice immunized with 2 microgram of Ag85B-ESAT6 in DDA/total lipids, DOTAP/total lipids, DC-Chol/ total lipids, neutral liposomes/total lipids, anionic liposomes/ total lipids or non-immunized naïve mice. Blood lymphocytes were isolated 5 weeks after the first immunization and re-stimulated in vitro with no antigen (control), Ag85B-ESAT (5, 0.5, 0.05 micrograms/millilitres).

FIG. 10. $Log_{10}$ resistance in the lungs and spleen of mice (n=6) immunized 3 months previously with Ag85B-ESAT6/DDA/purified apolar lipids (100, 10, 1, or 0.1 micrograms) or Ag85B-ESAT6/DDA/purified polar lipids (100, 10, or 1 micrograms). * Vaccines inducing significant protection compared to naïve, un-immunized mice ($p<0.05$).

FIG. 11. Release of IFN-gamma from blood lymphocytes isolated from naïve Balb/C mice or Balb/C mice immunized with Ag85B-ESAT6/DDA/total lipids from *M. bovis* BCG Russia, BCG Pasteur, *M. tuberculosis* H37Rv or BCG1331. Splenocytes were isolated 5 weeks after the first immunization, and the lymphocytes were stimulated with Ag85B-ESAT6 at 5 micrograms/millilitres).

REFERENCES

Andersen, P., D. Askgaard, L. Ljungqvist, M. W. Bentzon, and I. Heron. 1991. T-cell proliferative response to antigens secreted by *Mycobacterium tuberculosis*. Infect. Immun. 59:1558-1563.

Andersen, P. 1994. Effective vaccination of mice against *Mycobacterium tuberculosis* infection with a soluble mixture of secreted mycobacterial proteins. Infect. and Immun. 62:2536-2544.

Bangham, A. D., M. M. Standish and J. C. Watkins. 1965. Diffusion of univalent ions across lamellae of swollen phospholipids. J. Mol. Biol. 13: 238-252.

Bloom, B. R., and P. E. M. Fine. 1994. The BCG experience: Implications for future vaccines against tuberculosis., p. 531-557. In B. R. Bloom (ed.), Tuberculosis: Pathogenesis, protection and control. ASM Press, Washington D.C.

Brandt, L., M. Elhay, I. Rosenkrands, E. B. Lindblad, and P. Andersen. 2000. ESAT-6 subunit vaccination against *Mycobacterium tuberculosis*. Infect. Immun. 68:791-795.

Chang, C. D., and J. Meienhofer. 1978. Solid-phase peptide synthesis using a mild base cleavage of N alpha-fluorenylmethyloxycarbonylamino acids, exemplified by a synthesis of dihydrosomatostatin. Int. J. Pept. Protein Res. 11:246-249.

Collins, H. L., and S. H. Kaufmann. 2001. The many faces of host responses to tuberculosis. Immunology. 103:1-9.

Dascher, C. C., K. Hiromatsu, X. Xiong, C. Morehouse, G. Watts, G. Liu, D. N. McMurray, K. P. LeClair, S. A. Porcelli, and M. B. Brenner. 2003. Immunization with a mycobacterial lipid vaccine improves pulmonary pathology in the guinea pig model of tuberculosis. Int Immunol 15:915-25.

Dobson, G., D. E. Minnikin, S. M. Minnikin, J. H. Parlett, M. Goodfellow, M. Ridell, and M. Magnusson. 1985. Systematic analysis of complex mycobacterial lipids, p. 237-265. In M. Goodfellow, and D. E. Minnikin (ed.), Chemical methods in bacterial systematics, vol. 1. Academic Press, London.

Eriksson, K., M. Frederiksson, I. Nordstrom, and J. Holmgren. 2003. Cholera toxin and its B subunit promote dendritic cell vaccination with different influences on Th1 and Th2 development. Infect. Immun. 71:1740-7.

Folch, J., M. Lees, and G. H. S. Stanley. 1957. A simple method for the isolation and purification of total lipids from animal tissues. J. Biol. Chem. 226:497-509.

Glück, R. 1995. Liposomal presentation of antigens for human vaccines, p. 325-345. In M. F. Powell, and M. J. Newman (ed.), Vaccine design. The subunit and adjuvant approach. Plenum Press, New York.

Gregoriadis, G. 1995. Engineering liposomes for drug delivery: progress and problems. Trends Biotechnol. 13:527-37.

Gregoriadis, G., B. McCormack, M. Obrenovic, Y. Perrie, and R. Saffie. 2000. Liposomes as immunological adjuvants and vaccine carriers, p. 137-150. In D. T. O'Hagan (ed.), Vaccine adjuvants, vol. 42. Humana Press, Totowa.

Harboe, M., A. S. Malin, H. S. Dockrell, H. G. Wiker, G. Ulvund, A. Holm, M. C. Jorgensen, and P. Andersen. 1998. B-cell epitopes and quantification of the ESAT-6 protein of *Mycobacterium tuberculosis*. Infection and Immunity. 66:717-723.

Hilgers, L. A., and H. Snippe. 1992. DDA as an immunological adjuvant. Res Immunol. 143:494-503; discussion 574-6.

Hiu, I. J. 1975. Mycobacterial adjuvant and its carrier. Experientia. 31:983-5.

Holten-Andersen, L., T. M. Doherty, K. V. Knudsen, and P. Andersen. 2004. DDA/TDB—a Th1-inducing adjuvant formulation for TB subunit vaccines. Infect. Immun. 72: 1608-17.

Kensil, C. R., U. Patel, M. Lennick, and D. Marciani. 1991. Separation and characterization of saponins with adjuvant activity from *Quillaja saponaria* Molina cortex. J Immunol. 146:431-7.

Koike, Y., Y. C. Yoo, M. Mitobe, T. Oka, K. Okuma, S. Tonooka, and I. Azuma. 1998. Enhancing activity of mycobacterial cell-derived adjuvants on immunogenicity of recombinant human hepatitis B virus vaccine. Vaccine. 16:1982-9.

Lindblad, E. B., M. J. Elhay, R. Silva, R. Appelberg, and P. Andersen. 1997. Adjuvant modulation of immune response to tuberculosis sub-unit vaccines. Infection and Immunity. 65:623-629.

McBride, B. W., A. Mogg, J. L. Telfer, M. S. Lever, J. Miller, P. C. Turnbull, and L. Baillie. 1998. Protective efficacy of a recombinant protective antigen against *Bacillus anthracis* challenge and assessment of immunological markers. Vaccine. 16:810-7.

Moingeon, P., J. Haensler, and A. Lindberg. 2001. Towards the rational design of Th1 adjuvants. Vaccine. 19:4363-72.

Olsen, A. W., L. A. H. vanPinxteren, L. M. Okkels, P. B. Rasmussen, and P. Andersen. 2001. Protection of mice with a tuberculosis subunit vaccine based on a fusion protein of antigen 85B and ESAT-6. Infect. Immun. 69:2773-2778.

Peltoniemi, J., N. Setala, E. Broberg, M. Roytta, V. Hukkanen, A. A. Salmi, and J. P. Eralinna. 2002. Semliki Forest virus infection is enhanced in Th1-prone SJL mice but not in Th2-prone BALB/c mice during Linomide-induced immunomodulation. J Neuroimmunol. 132:83-92.

Saito, R., A. Tanaka, K. Sugiyama, I. Azuma, and Y. Yamamura. 1976. Adjuvant effect of cord factor, a mycobacterial lipid. Infect. Immun. 13:776-81.

Siders, W. M., K. Vergillis, C. Johnson, R. K. Scheule, and J. M. Kaplan. 2002. Tumor treatment with complexes of cationic lipid and noncoding plasmid DNA results in the induction of cytotoxic T cells and systemic tumor elimination. Mol Ther. 6:519-27.

Spector, D. J., and Samaniego, L. A. 1995. Construction and isolation of recombinant adenovirus wuth gene replacements. Methods in Molecular Genetics. 7:31-44.

Stanfield, J. P., D. Gall, and P. M. Bracken. 1973. Single-dose antenatal tetanus immunisation. Lancet. 1:215-9.

Suzuki, F., R. R. Brutkiewicz, and R. B. Pollard. 1986. Importance of Lyt 1+ T-cells in the antitumor activity of an immunomodulator, SSM, extracted from human-type Tubercle bacilli. J Natl Cancer Inst. 77:441-7.

Theisen, M., S. Soe, K. Brunstedt, F. Follmann, L. Bredmose, H. Israelsen, S. M. Madsen, And P. Druilhe. 2004. A *Plasmodium falciparum* GLURP-MSP3 chimeric protein; expression in *Lactococcus lactis*, immunogenicity and induction of biologically active antibodies. Vaccine 22: 1188-89.

Yamazaki, S., K. Koyama, S. Someya, I. Azuma, and Y. Yamamura. 1969. Studies on the allergenicity of various tuberculoprotein derivatives and the adjuvanticity of wax D fractions of *Mycobacterium tuberculosis*. Am Rev Respir Dis. 100:691-8.

van Rooij, E. M., H. L. Glansbeek, L. A. Hilgers, E. G. to Lintelo, Y. E. de Visser, W. J. Boersma, B. L. Haagmans, and A. T. Bianchi. 2002. Protective antiviral immune responses to pseudorabies virus induced by DNA vaccination using dimethyldioctadecylammonium bromide as an adjuvant. J Virol. 76:10540-5.

Wang, J., A. Zganiacz, and Z. Xing. 2002. Enhanced immunogenicity of BCG vaccine by using a viral-based GM-CSF transgene adjuvant formulation. Vaccine. 20:2887-98.

WO 03/011336. Sprott, D., L. Krishnan, and S. Sad. Vaccine adjuvant properties of liposomes formed at elevated temperatures from the polar chloroform extractable lipids from *Mycobacterium bovis* Bacillus Calmette-Guerin.

The invention claimed is:

1. A method of increasing the immune response to an antigenic component, comprising administering a vaccine comprising an adjuvant and an antigenic component to a subject; and observing an increased immune response as compared to control subjects;

wherein said adjuvant comprises dimethyldioctadecylammonium-bromide, -chloride, -phosphate or -acetate (DDA) and an apolar fraction or part of said apolar fraction of a total lipid extract of a mycobacterium;

wherein the proportion of lipids in said apolar fraction and in said part of the apolar fraction which are glycolipids, is lower than that of lipids in said total lipid extract.

2. The method of claim 1, wherein said apolar fraction and said part of an apolar fraction being essentially free of glycoplipids.

3. The method of claim 1, wherein the proportion of lipids in said apolar fraction and in said part of the apolar fraction which are glycolipids of intermediate polarity, is lower than that of lipids in said total lipid extract.

4. The method according to claim 3, wherein said apolar fraction and said part of the apolar fraction is essentially free of glycoplipids of intermediate polarity.

5. The method according to claim 1, wherein the proportion of lipids in said apolar fraction and in said part of the apolar fraction which are trehalose dimycolate, is lower than that of lipids in said total lipid extract.

6. The method according to claim 5, wherein said apolar fraction and said part of the apolar fraction is essentially free of trehalose dimycolate.

7. The method according to claim 1, wherein the proportion of lipids in said apolar fraction and in said part of the apolar fraction which are triacylated pentamannosides, tetracylated pentamannosides, triacylated dimannosides, tetracylated dimannosides, phosphatidylinositols, phosphatidylethanolamines or diphosphatidylglycerols, is lower than that of lipids in said total lipid extract.

8. The method according to claim 1, wherein said apolar fraction comprises phthiocerol dimycoserosate and triacylglycerol.

9. The method according to claim 1, wherein said total lipid extract is obtained by extraction with Chloroform/Methanol (2:1).

10. The method according to claim 1, wherein said immune response is a cellular immune response.

11. The method according to claim 1, wherein said immune response is release of interferon-γ (IFN-γ).

12. The method according to claim 10, wherein said immune response further comprises a humoral immune response.

13. The method according to claim 11, wherein said immune response further comprises an antibody response.

14. The method according to claim 1, wherein said antigenic component is a polypeptide or an immunogenic portion thereof.

* * * * *